United States Patent
Klimyuk et al.

(10) Patent No.: US 7,667,092 B2
(45) Date of Patent: Feb. 23, 2010

(54) PROCESSES AND VECTORS FOR AMPLIFICATION OR EXPRESSION OF NUCLEIC ACID SEQUENCES OF INTEREST IN PLANTS

(75) Inventors: Victor Klimyuk, Halle/Saale (DE); Yuri Gleba, Halle/Saale (DE); Mario Gils, Halle/Saale (DE); Maxim Skulachev, Moscow (RU); Sylvestre Marillonet, Halle/Saale (DE)

(73) Assignee: Icon Genetics GmbH, Munich (DE)

( * ) Notice: Subject to any disclaimer, the term of this patent is extended or adjusted under 35 U.S.C. 154(b) by 854 days.

(21) Appl. No.: 10/476,299

(22) PCT Filed: Mar. 27, 2002

(86) PCT No.: PCT/EP02/03476

§ 371 (c)(1),
(2), (4) Date: Jun. 24, 2004

(87) PCT Pub. No.: WO02/088369

PCT Pub. Date: Nov. 7, 2002

(65) Prior Publication Data

US 2004/0255347 A1    Dec. 16, 2004

(30) Foreign Application Priority Data

Apr. 30, 2001 (DE) ................ 101 21 283

(51) Int. Cl.
*C12N 15/82* (2006.01)
*C12N 15/83* (2006.01)

(52) U.S. Cl. ..................................... 800/278
(58) Field of Classification Search ............... None
See application file for complete search history.

(56) References Cited

U.S. PATENT DOCUMENTS

| | | | |
|---|---|---|---|
| 5,139,812 A | 8/1992 | Lebacq | |
| 5,316,931 A | 5/1994 | Donson et al. | |
| 5,466,788 A | 11/1995 | Ahlquist et al. | |
| 5,474,925 A | 12/1995 | Maliyakal et al. | |
| 5,576,198 A | 11/1996 | McBride et al. | |
| 5,627,059 A | 5/1997 | Capecchi et al. | |
| 5,670,353 A | 9/1997 | Ahlquist et al. | |
| 5,670,623 A | 9/1997 | Shoseyov et al. | |
| 5,723,765 A | 3/1998 | Oliver et al. | |
| 5,801,030 A | 9/1998 | McVey et al. | |
| 5,866,785 A | 2/1999 | Donson et al. | |
| 5,877,402 A | 3/1999 | Maliga et al. | |
| 5,889,190 A | 3/1999 | Donson et al. | |
| 6,100,448 A | 8/2000 | Thompson et al. | |
| 6,147,278 A | 11/2000 | Rogers et al. | |
| 6,174,700 B1 | 1/2001 | Haynes et al. | |
| 6,300,545 B1 | 10/2001 | Baszczynski et al. | |
| 6,331,416 B1 | 12/2001 | Shani et al. | |
| 6,331,661 B1 | 12/2001 | Baszczynski et al. | |
| 6,781,033 B2 | 8/2004 | Staub et al. | |
| 2003/0188337 A1 | 10/2003 | Day et al. | |
| 2004/0055037 A1 | 3/2004 | Gleba et al. | |
| 2004/0083499 A1 | 4/2004 | Eibl et al. | |
| 2004/0088764 A1 | 5/2004 | Gleba et al. | |
| 2004/0137631 A1 | 7/2004 | Herz et al. | |
| 2004/0191788 A1 | 9/2004 | Gleba et al. | |
| 2004/0221330 A1 | 11/2004 | Klimyuck et al. | |
| 2004/0244073 A1 | 12/2004 | Klimyuck et al. | |
| 2004/0255347 A1 | 12/2004 | Klimyuck et al. | |
| 2005/0014150 A1 | 1/2005 | Atabekov et al. | |
| 2005/0015829 A1 | 1/2005 | Koop et al. | |
| 2005/0015830 A1 | 1/2005 | Dorokhov et al. | |
| 2005/0059004 A1 | 3/2005 | Atabekov et al. | |
| 2005/0066384 A1 | 3/2005 | Klimyuck et al. | |
| 2005/0091706 A1 | 4/2005 | Klimyuck et al. | |

FOREIGN PATENT DOCUMENTS

| | | |
|---|---|---|
| EP | 0270 248 | 6/1988 |
| EP | 1 045 037 | 10/2000 |
| WO | WO 87/00551 | 1/1987 |
| WO | WO 94/16089 | * 7/1994 |
| WO | WO 95/34668 | 12/1995 |
| WO | WO 96/17954 | 6/1996 |
| WO | WO 98/09505 | 3/1998 |
| WO | WO 98/44097 | 10/1998 |
| WO | WO 98/54342 | 12/1998 |
| WO | WO 99/25821 | 5/1999 |

(Continued)

OTHER PUBLICATIONS

Vergunst et al. Cre/lox-mediated site-specific integration of Agrobacterium T-DNA in Arabidopsis thaliana by transient expression of cre. (1998) PMB, vol. 38, pp. 393-406.*

Peterson-Burch et al., Trends in Genetics, 2000, vol. 16, pp. 151-152.*

Derbyshire et al. "Lightning strikes twice: Intron-intein coincidence" *Proc. Natl. Acad. Sci. USA* 95:1356-1357 (1998).

Lustig et al. "Long Poly(A) Tracts in the Human Genome are Associate with the *Alu* Family of Repeated Elements" *J. Mol. Biol.* 180:753-759 (1984).

(Continued)

*Primary Examiner*—Ashwin Mehta
(74) *Attorney, Agent, or Firm*—Myers Bigel Sibley & Sajovec, P.A.

(57) ABSTRACT

This invention discloses a biologically safe process of causing amplification and/or expression of one or more nucleic acid sequences of interest in a plant, plant tissue, plant cell or cell culture, characterized in that a plant cell is provided with at least two precursor vectors designed for undergoing processing by site-specific recombination in said cell, whereby due to said processing said plant cell is endowed with at least one replicon which provide(s) for said amplification and/or expression.

24 Claims, 23 Drawing Sheets

FOREIGN PATENT DOCUMENTS

| WO | WO 99/25855 | 5/1999 |
|---|---|---|
| WO | WO 99/36516 | 7/1999 |
| WO | WO 01/11020 | 2/2000 |
| WO | WO 00/17365 | 3/2000 |
| WO | WO 00/20611 | 4/2000 |
| WO | WO 00/32799 | 6/2000 |
| WO | WO 00/52187 A2 | 9/2000 |
| WO | WO 00/68391 | 11/2000 |
| WO | WO 00/68431 | 11/2000 |
| WO | WO 00/70019 | 11/2000 |
| WO | WO 00/77174 | 12/2000 |
| WO | WO 00/77175 | 12/2000 |
| WO | WO 00/78985 | 12/2000 |
| WO | WO 01/55369 | 8/2001 |
| WO | WO 01/59138 | 8/2001 |
| WO | WO 01/81600 | 11/2001 |
| WO | WO 02/12522 | 2/2002 |
| WO | WO 02/29068 | 4/2002 |
| WO | WO 02/46438 | 6/2002 |
| WO | WO 02/46440 | 6/2002 |
| WO | WO 02/055651 | 7/2002 |
| WO | WO 02/057466 | 7/2002 |
| WO | WO 02/068664 | 9/2002 |
| WO | WO 02/077246 | 10/2002 |
| WO | WO 02/079481 | 10/2002 |
| WO | WO 02/088369 | 11/2002 |
| WO | WO 02/101060 | 12/2002 |
| WO | WO 03/001900 | 1/2003 |
| WO | WO 03/004658 | 1/2003 |
| WO | WO 03/020927 | 3/2003 |
| WO | WO 03/020928 | 3/2003 |
| WO | WO 03/020938 | 3/2003 |

OTHER PUBLICATIONS

Wu et al. "Markerless Deletions of *pil* Genes in *Myxococcus xanthus* generated by Counterselection with the *Bacillus subtilis sacB* Gene" *Journal of Bacteriology* 178(19):5817-5281 (1996).

Hagemann et al. "Extranuclear Inheritance: Plastid Genetics" *Progress in Botany*, vol. 55, 260-275 (1994).

Klaus et al. "Generation of Marker Free Plastid Transformants Using a Transiently Cointegrated Selection Gene" *Nature Biotechnology* 22: 225-229 (2004).

Mühlbauer et al. "Functional analysis of plastid DNA replication origins in tobacco by targeted inactivation" *The Plant Journal*, 32:175-184 (2002).

Parry et al. "Construction of a bidirectional promoter probe vector and its use in analyzing *nod* gene expression in *Rhizobium loti*." *Gene*, 150: 105-109 (1994).

Ruf et al. "Stable Genetic Transformation of Tomato Plastids and Expression of a Foreign Protein in Fruit" *Nature Biotechnology* 19: 870-875 (2001).

Sanz et al. "Altered local and systemic spread of movement deficient virus in transgenic tobacco plants expressing the cucumber mosaic virus 3a protein" Arch Virol. 145:2387-2401 (2000).

Shimada et al. "Fine Structural Features of the Chloroplast Genome: Comparison of the Sequenced Chloroplast Genomes" *Nucleic Acids Research* 19: 983-995 (1991).

Shinozaki et al. "The Complete Nucleotide Sequence of the Tobacco Chloroplast Genome: Its Gene Organization and Expression" *The EMBO Journal* 5: 2043-2049 (1986).

Sidorov et al. "Stable Chloroplast Transformation in Potato: Use of Green Fluorescent Protein as a Plastid Marker" *The Plant Journal* 19: 209-216 (1999).

Attal et al., "The efficiency of different IRESs (Internal Ribosomes Entry Site) in monocistronic mRNAs," *Molecular Biology Reports* 27: 21-26 (2000).

Skulachev et al., "Internal Initiation of Translation Directed by the 5'-Untranslated Region of the Tobamovirus Subgenomic RNA $I_2$," *Virology* 263: 139-154 (1999).

Donson et al. "Systemic expression of a bacterial gene by a tobacco mosaic" *Proc. Natl. Acad. Sci. USA* 88: 7204-7208 (1991).

Murakami et al. "High-level expression of exogenous genes by replication-competent retrovirus vectors with an internal ribosomal entry site" *Gene* 202: 23-29 (1997).

Porta et al. "Use of Viral Replicons for the Expression of Genes in Plants" *Molecular Biotechnology* 5:209-221 (1996).

Vergunst et al. "Cre/*lox*-mediated site-specific integration of *Agrobacterium* T-DNA in *Arabidopsis thaliana* by transient expression of *cre*" *Plant Molecular Biology* 38:393-406 (1998).

Zhao et al. "Development and evaluation of a complementation-dependent gene delivery system based on cucumber mosaic virus" *Arch Virol* 145:2285-2295 (2000).

International Search Report for International Application Serial No. PCT/EP02/03476, mailed Oct. 21, 2002.

Albert et al. (1995) "Site-specific integration of DNA into wild-type and mutant lox sites placed in the plant genome" The Plant Journal 7:649-659.

Allison et al., "Deletion of rpoB Reveals a Second Distinct Transcription System in Plastids of Higher Plants," The EMBO Journal, 15:11 2802-2809 (1996).

Altschul et al. "Basic Local Alignment Search Tool," J. Mol. Biol., 215:403-410 (1990).

Anandalakshmi et al. (1998) "A viral suppressor of gene silencing in plants" Proc. Natl. Acad. Sci. U.S.A. 95:13079-13084.

Anandalakshmi et al. (2000) "A calmodulin-related protein that suppresses posttranscriptional gene silencing in plants" Science 290:142-144.

Arnold et al. "Allelic Ladder, D18S51 Allele 8" EBI Database accession No. AAX01351 (Apr. 14, 1999) Abstract.

Bagwell, BC "Poly-dA 50mer Probe Target Sequence" EBI Database accession No. AAQ66922 (Jan. 24, 1995) Abstract.

Bateman et al. (2000) "Tools for chloroplast transformation in Chlamydomonas: expression vectors and a new dominant selectable marker" Mol. Gen. Genet. 263:401-410.

Bergamini et al. "Picornavirus IRESes and the Poly(A) tail Jointly Promote Cap-Independent Translation in a Mammalian Cell-free System," RNA, 6:1781-1790 (2000).

Bogorad, Lawrence, "Engineering Chloroplasts: an Alternative Site for Foreign Genes, Proteins, Reactions and Products," TIBTECH, 18:257-263 (Jun. 2000).

Bouchez et al. (1993) "A binary vector based on Basta resistance for in planta transformation of Arabidopsis thaliana" C. R. Acad. Sci. Paris, Science de la vie 316:1188-1193.

Boynton et al., "Chloroplast Transformation in Chlamydomonas with High Velocity Microprojectiles," Science, 240:1534-1538 (1988).

Carpin et al. (2001) "Identification of a Ca2+-Pectate Binding Site on an Apoplastic Peroxidase" The Plant Cell 13:511-520.

Chappell et al. "A 9-nt Segment of Cellular mRNA Can Function as an Internal Ribosome Entry Site (IRES) and When Present In Linked Multiple Copies Greatly Enhances IRES Activity," PNAS, 97(4):1536-1541 (Feb. 15, 2000).

Clelland et al. (1999) "Hiding Messages in DNA Microdots," Nature 399:533-534.

Coutts et al. "Development of Geminivirus-based Gene Vectors for Dicotyledonous Plants" Australian Journal of Plant Physiology 17:365-375 (1990).

Dale et al. "Intra- and intermolecular site-specific recombination in plant cells mediated by bacteriophage P1 recombinase" Gene 91:79-85 (1990).

Dale et al. "Mutations in the CRE/LOX Recombination Site Enhance the Stability of Recombination Products: Applications for Gene Targeting in Plants" Journal of Cellular Biochemistry 50 (S16S):206 (1992).

Daniell, "New Tools for Chloroplast Genetic Engineering," Nature Biotechnology, 17:855-856 (Sep. 1999).

De Santis-Maciossek et al., "Targeted Disruption of the Plastid RNA Polymerase Genes rpoA, B and C1: Molecular Biology, Biochemistry and Ultrastructure," The Plant Journal, 18(5):477-489 (1999).

Domingo et al. (1999) "Identification of a novel peptide motif that mediates cross-linking of proteins to cell walls" The Plant Journal 20:563-570.

Dorokhov et al. "Polypurine (A)-Rich Sequences Promote Cross-Kingdom Conservation of Internal Ribosome Entry" PNAS 99(8):5301-5306 (Apr. 16, 2002).

Drescher et al., "The Two Largest Chloroplast Genome-Encoded Open Reading Frames of Higher Plants are Essential Genes," The Plant Journal, 22(2):97-104 (2000).

El-Sheekh, M.M. (2000) "Stable Chloroplast Transformation in *Chlamydomonas reinhardtii* using Microprojectile Bombardment" Folia Microbiol. 45(6) 496-504.

Fischer et al., "Selectable Marker Recycling in the Chloroplast," Mol. Gen. Genet., 251:373-380 (1996).

Gatz et al. (1991) "Regulation of a modified CaMV 35S promoter by the Tn10-encoded Tet repressor in transgenic tobacco" Mol. Gen. Genet. 227:229-237.

Hager at al., "Enslaved Bacteria as New Hope for Plant Biotechnologists," Appl. Microbiol. Biotechnol., 54:302-310 (2000).

Heifetz, Peter B., "Genetic Engineering of the Chloroplast," Biochimie, 82:655-666 (2000).

Hoff et al. (2001) "A recombinase-mediated transcriptional induction system in transgenic plants" Plant Mol. Biol. 45:41-49.

Horvath et al., "Targeted Inactivation of the Plastid ndhB Gene in Tobacco Results in an Enhanced Sensitivity of Photosynthesis to Moderate Stomatal Closure," Plant Physiology, 123:1337-1349 (Aug. 2000).

Houdebine et al. "Internal Ribosome Entry Sites (IRESs): Reality and Use" Transgenic Research, 8:157-177 (1999).

Iamtham et al. (2000) "Removal of antibiotic resistance genes from transgenic tobacco plastids" 18:1172-1176.

Ivanov et al. "A Tobamovirus Genome That Contains an Internal Ribosome Entry Site Functional In Vitro," Virology, 232:32-43 (1997).

Jeon et al. (2000) "T-DNA insertional mutagenesis for functional genomics in rice" Plant J. 22:561-570.

Kofer et al., "PEG-Mediated Plastid Transformation in Higher Plants," In Vitro Cell. Dev. Biol.- Plant, 31:303-309 (1998).

Koshinsky et al. (2000) "Cre-lox site-specific recombination between Arabidopsis and tobacco chromosomes" The Plant Journal 23:715-722.

Kozak, "Initiation of Translation in Prokaryotes and Eukaryotes" Gene 234:187-208 (1999).

Kumagai et al. (1995) "Cytoplasmic inhibition of carotenoid biosynthesis with virus-derived DNA" Proc. Natl. Acad. Sci. USA 92:1679-1683.

Lehtiö et al. (2001) "Directed immobilization of recombinant staphylococci on cotton fibers by functional display of a fungal cellulose-binding domain" FEMS Microbiology Letters 195:197-204.

Lopez de Quinto et al. "Parameters Influencing Translational Efficiency in Aphthovirus IRES-Based Bicistronic Expression Vectors" Gene 217:51-56 (1998).

Martinez-Salas, Encarnacion. "Internal Ribosome Entry Site Biology and Its Use in Expression Vectors," Current Opinion in Biotechnology, 10:458-464 (1999).

Matzk et al. (1994) "Improved Techniques for haploid Production in Wheat using Chromosome Elimination" Plant Breeding 113:125-129.

Melchers et al (1974) "Somatic Hybridisation of Plants by Fusion of Protoplasts" Molec. Gen. Genet. 135:277-294.

Michael et al. (1999) "Efficient gene-specific expression of Cre recombinase in the mouse embryo by targeted insertion of a novel IRES-Cre cassette into endogenous loci" Mech. Dev. 85:35-47.

Mizuguchi et al. (2000) "IRES-Dependent Second Gene Expression Is Significantly Lower Than Cap-Dependent First Gene Expression in a Bicistronic Vector" Mol. Ther. 1:376-382.

Monde et al., "Post-Transcriptional Defects in Tobacco Chloroplast Mutants Lacking the Cytochrome b6/f Complex," The Plant Journal, 21(1):61-72 (2000).

Mountford et al. (1995) "Internal ribosome entry sites and dicistronic RNAs in mammalian transgenesis" Trends Genet. 11:179-184.

Niepel et al. (1999) "Identification and Characterization of the Functional Elements within the Tobacco Etch Virus 5' Leader Required for Cap-Independent Translation" J. Virol. 73:9080-9088.

Neunzig et al. "Self replicating vectors as a tool for gene targeting in plants" Experienta 46:A34 (1990).

Owens et al. "Identification of Two Short Internal Ribosome Entry Sites Selected From Libraries of Random Oligonucleotides," PNAS, 98(4):1471-1476 (Feb. 13, 2001).

Pearson et al. "Improved Tools for Biological Sequence Comparison," Proc. Nat'l. Acad. Sci. USA, 85: 2444-2448 (Apr. 1988).

Peterson-Burch et al. "Retroviruses in plants?" Trends in Genetics 16:151-152 (2000).

Preiss et al. "Dual Function of the Messenger RNA Cap Structure in Poly(A)-tail-promoted Translation In Yeast," Nature, 392:516-520 (Apr. 2, 1998).

Qin et al. (Mar. 1994) "Cre recombinase-mediated site-specific recombination between plant chromosomes" Proc. Natl. Acad. Sci. 91:1706-1710.

Riera-Lizarazu et al. (1993) "Polyhaploid Production in the Triticeae: Wheat x Tripsacum Crosses" Crop Science 33:973-976.

Ruf et al., "Targeted Inactivation of a Tobacco Intron-Containing Open Reading Frame Reveals a Novel Chloroplast-Encoded Photosystem I-Related Gene," The Journal of Cell Biology, 139(1):95-102 (Oct. 6, 1997).

Schreuder et al. (1993) "Targeting of a Heterologous Protein to the Cell Wall of *Saccharomyces cerevisiae*" Yeast 9:399-409.

Serino et al., "RNA Polymerase Subunits Encoded by the Plastid rpo Genes are Not Shared with the Nucleus-Encoded Plastid Enzyme," Plant Physiol., 117:1165-1170 (1998).

Shepard et al. (1983) "Genetic Transfer in Plants Through Interspecific Protoplast Fusion" Science 219:683-688.

Stanley, J. "Geminiviruses: plant viral vectors" Current Opinion in Genetics and Development 3:91-96 (1993).

Staub et al. (1994) "Extrachromosomal elements in tobacco plastids" Proc. Natl. Acad. Sci. 91:7468-7472.

Staub et al., "Expression of a Chimeric uidA Gene Indicates that Polycistronic mRNAs are Efficiently Translated in Tobacco Plastids," The Plant Journal, 7(5):845-848 (1995).

Suzuki et al. (1997) "Generation and maintenance of tandemly repeated extrachromosomal plasmid DNA in Chlamydomonas chloroplasts" Plant J. 11:635-648.

Suzuki et al., "Engineering of the rp123 Gene Cluster to Replace the Plastid RNA Polymerase α Subunit with the *Escherichia Coli* Homologue," Curr. Genet., 38:218-225 (2000).

Toth et al. (2001) "A novel strategy for the expression of foreign genes from plant virus vectors" FEBS Lett. 489:215-219.

Ueda et al. (2000) "Genetic immobilization of proteins on the yeast cell surface" Biotechnology Advances 18:121-140.

Urwin et al. (2000) "Functional characterization of the EMCV IRES in plants" Plant J. 24:583-589.

Valancius et al. (1991) "Testing an "In-Out" Targeting Procedure for Making Subtle Genomic Modifications in Mouse Embryonic Stem Cells" Molecular and Cellular Biology 11:1402-1408.

Van Haaren et al. (1993) "Prospects of applying a combination of DNA transposition and site-specific recombination in plants: a strategy for gene identification and cloning" Plant Molecular Biology 23:525-533.

Walden et al. "Gene-transfer and plant regeneration techniques" Trends in Biotechnology 13:324-331 (1995).

Wells et al. (1999) "Codon optimization, genetic insulation, and rtTA reporter improve performance of the tetracycline switch" Transgenic Res. 8:371-381.

Whitney et al., "Directed Mutation of the Rubisco Large Subunit of Tobacco Influences Photorespiration and Growth," Plant Physiology, 121:579-588 (Oct. 1999).

Wilde et al. (1992) "Control of gene expression in tobacco cells using a bacterial operator-repressor system" EMBO J. 11:1251-1259.

International Search Report for International Application Serial No. PCT/EP01/11629, mailed Jun. 3, 2002.

International Search Report for International Application Serial No. PCT/EP02/02091, mailed Jun. 19, 2002.

International Search Report corresponding to PCT/EP01/15034; Date of Mailing: Jun. 19, 2002.

International Search Report for International Application Serial No. PCT/EP 02/07134 dated Jun. 27, 2002.

International Search Report corresponding to PCT/EP02/06464; Date of Mailing: Sep. 30, 2002.

International Search Report for International Application Serial No. PCT/EP01/14421, mailed Nov. 29, 2002.

International Search Report corresponding to PCT/EP02/03266; Date of Mailing: Feb. 18, 2003.

International Search Report corresponding to PCT/EP02/09843, mailed May 21, 2003.

International Search Report mailed on Jun. 8, 2003 for application No. PCT/EP EP 02/09605.

International Search Report mailed on Jul. 14, 2003 for application No. PCT/EP EP 02/04777.

International Search Report for application No. PCT/EP02/09844, mailed Jul. 15, 2003.

* cited by examiner

Step 1
Cloning of KpnI/XhoI and
XhoI/HindIII-fragments of plasmid
pICH3461 into HindIII/KpnI-sites of
plasmid pICBV10 pICH3461 pICBV10

Resulting plasmid:
pICH4371 pICP1010

PROCESSES AND VECTORS FOR AMPLIFICATION OR EXPRESSION OF NUCLEIC ACID SEQUENCES OF INTEREST IN PLANTS

CROSS-REFERENCE TO RELATED APPLICATIONS

The present application is a 35 U.S.C. § 371 National Phase Application of International Application Serial No. PCT/EP02/03476, filed Mar. 27, 2002 and published in English as PCT Publication No. WO 02/088369 on Nov. 7, 2002, which claims priority to German Patent Application Serial No. 101 21 283.6, filed Apr. 30, 2001, the disclosures of each of which are incorporated herein by reference in their entireties.

FIELD OF THE INVENTION

The present invention relates to processes and vectors for causing amplification or expression of one or more nucleic acid sequences of interest in a plant cell.

BACKGROUND OF THE INVENTION

Significant progress in plant biotechnology during the last two decades has opened the opportunities for commercial scale molecular farming in plants. The production of recombinant proteins in plants is an attractive alternative to more traditional systems based on bacteria and yeasts. It has an obvious advantage over the existing systems built on fermenters production due to its lower cost and the easiness of upscaling the production by simply increasing the harvesting of plant biomass.

In general, molecular farming in plants can be achieved by stable or transient expression of a recombinant protein of interest (Franken et al., 1997, *Curr. Opin. Biotechnol.*, 8, 411-416; Fischer et al., 1999, *Biotechnol. Appl. Biochem.*, Pt 2, 101-108; Herbers & Sonnewald, 1999, *Curr. Opin. Biotechnol*, 10 163-168). Stable transgenic plants can be used to produce vegetative tissues or seeds rich in recombinant protein. Vegetative tissue can be used directly for the processing while the seeds are more suitable for long-term storage. However, to reach high level of protein expression in plants is not an ordinary task, especially for the production of proteins compromising the plant growth. It requires the development of appropriately regulated expression systems, thus allowing to switch on the protein production at the right stage of plant development.

Existing technologies for controlling gene expression in plants are usually based on tissue-specific and inducible promoters and practically all of them suffer from a basal expression activity even when uninduced, i.e. they are "leaky". Tissue-specific promoters (U.S. Pat. No. 5,955,361; WO09828431) present a powerful tool but their use is restricted to very specific areas of applications, e.g. for producing sterile plants (WO9839462) or expressing genes of interest in seeds (WO00068388; U.S. Pat. No. 5,608,152). Inducible promoters can be divided into two categories according to their induction conditions—those induced by abiotic factors (temperature, light, chemical substances) and those that can be induced by biotic factors, for example, pathogen or pest attack. Examples of the first category are heat-inducible (U.S. Pat. No. 5,187,287) and cold-inducible (U.S. Pat. No. 5,847,102) promoters, a copper-inducible system (Mett et al., 1993, *Proc. Natl. Acad. Sci.*, 90, 4567-4571), steroid-inducible systems (Aoyama & Chua, 1997, *Plant J.*, 11, 605-612; McNellis et al., 1998, *Plant J.*, 14, 247-257; U.S. Pat. No. 6,063,985), an ethanol-inducible system (Caddick et al., 1997, *Nature Biotech.*, 16, 177-180; WO09321334), and a tetracycline-inducible system (Weinmann et al., 1994, *Plant J.*, 5, 559-569). One of the latest developments in the area of chemically inducible systems for plants is a chimaeric promoter that can be switched on by glucocorticoid dexamethasone and switched off by tetracycline (Bohner et al., 1999, *Plant J.*, 19, 87-95). For a review on chemically inducible systems see: Zuo & Chua, (2000, *Current Opin. Biotechnol*, 11, 146-151). Other examples of inducible promoters are promoters which control the expression of patogenesis-related (PR) genes in plants. These promoters can be induced by treatment of the plant with salicylic acid, an important component of plant signaling pathways in response to pathogen attack, or other chemical compounds (benzo-1,2,3-thiadiazole or isonicotinic acid) which are capable of triggering PR gene expression (U.S. Pat. No. 5,942,662).

There are reports of controllable transgene expression systems using viral RNA/RNA polymerase provided by viral infection (for example, see U.S. Pat. Nos. 6,093,554; 5,919, 705). In these systems, a recombinant plant DNA sequence includes the nucleotide sequences from the viral genome recognized by viral RNA/RNA polymerase. The effectiveness of these systems is limited because of the low ability of viral polymerases to provide functions in trans and their inability to control processes other than RNA amplification.

The systems described above are of significant interest as opportunities of obtaining desired patterns of transgene expression, but they do not allow tight control over the expression patterns, as the inducing agents (copper) or their analogs (brassinosteroids in case of steroid-controllable system) can be present in plant tissues at levels sufficient to cause residual expression. Additionally, the use of antibiotics and steroids as chemical inducers is not desirable for the large-scale applications. When using promoters of PR genes or viral RNA/RNA polymerases as control means for transgenes the requirements of tight control over transgene expression are also not fulfilled, as casual pathogen infection or stress can cause expression. The tissue or organ-specific promoters are restricted to very narrow areas of applications, since they confine expression to a specific organ or stage of plant development, but do not allow the transgene to be switched on at will.

One way of achieving high level of protein production is transient expression, where the transgene can be delivered and expressed at the desired stage of plant development, fully exploiting plant resources and allowing high yield of the desired product. The transient expression approach most suitable for medium to large-scale production include *Agrobacterium*-mediated (Kapila et al., 1996, *Plant Sci.*, 122, 101-108) and plant viral vector-mediated systems (for review see: Porta & Lomonossoff, 1996, *Mol. Biotechnol.*, 5, 209-221; Yusibov et al., 1999, *Curr. Top. Microbiol. Immunol.*, 240, 81-94). Viral vector-based expression systems offer a significantly higher yield of transgene product compared to plant nuclear transgenes. For example, the level of transgenic protein can reach 5-10% of the total cellular plant protein content, when expressed from a viral vector (Kumagai et al., 2000, *Gene*, 245, 169-174; Shivprasad et al., 1999, *Virology*, 255, 312-323). RNA viruses are the most suitable as they offer a higher expression level compared to DNA viruses. There are several published patents which describe viral vectors suitable for systemic expression of transgenic material in plants (U.S. Pat. Nos. 5,316,931; 5,589,367; 5,866,785). In general, these vectors can express a foreign gene as a translational fusion with a viral protein (U.S. Pat. Nos. 5,491,076; 5,977,438), from an additional subgenomic promoter (U.S.

Pat. Nos. 5,466,788; 5,670,353; 5,866,785), or from polycistronic viral RNA using IRES elements for independent protein translation (German Patent Application No. 10049587.7, PCT application PCT/EP01/11629). The first approach—translational fusion of a recombinant protein with a viral structural protein (Hamamoto et al., 1993, *BioTechnology*, 11, 930-932; Gopinath et al., 2000, *Virology*, 267, 159-173; JP6169789; U.S. Pat. No. 5,977,438) gives significant yield. However, the use of such an approach is limited, as the recombinant protein cannot be easily separated from the viral one. One of the versions of this approach employs the translational fusion via a peptide sequence recognized by a viral site-specific protease or via a catalytic peptide (Dolja et al., 1992, *Proc. Natl. Acad. Sci. USA*, 89, 10208-10212; Gopinath et al., 2000, *Virology*, 267, 159-173; U.S. Pat. Nos. 5,162,601; 5,766,885; 5,491,076).

Expression processes utilizing viral vectors built on heterologous subgenomic promoters provide the highest level of protein production to date (U.S. Pat. No. 5,316,931). The most serious disadvantage of such vectors and many others is their limited capacity with regard to the size of DNA to be amplified. Usually, stable constructs accommodate inserts of not more than one kb. In some areas of plant functional genomics this may not be such a serious limitation as G. della-Cioppa et al. (WO993651) described the use of TMV-based viral vectors to express plant cDNA libraries with the purpose of silencing endogenous genes. Two-component amplification systems which make use of helper viruses may offer a slightly better capacity (U.S. Pat. No. 5,889,191). However, for most applications, including production of proteins or low-molecular weight compounds in plants, these limitations cannot be remedied within existing processes. For example, in order to produce biodegradable plastics in plants, up to four recombinant genes must be expressed (Hanley et al., 2000, *Trends Plant Sci.*, 5, 45-46) and at least seven bacterial genes are required for modulation of the mevalonate biosynthetic pathway in plants (Dewick, P., 1999, *Nat. Prod. Rep.*, 16, 97-130).

A further serious concern with prior art virus-based plant expression systems is biological safety. On the one hand, high infectivity of the recombinant virus is highly desired in order to facilitate spread of the virus throughout the plant and to neighboring plants thereby increasing the yield of the desired gene product. On the other hand, such a high infectivity compromises containment of the recombinant material since spread to undesired plants may easily occur. Consequently, safer virus-based plant expression systems are highly desired.

Therefore, it is an object of the invention to provide a process of amplification or expression of a nucleic acid sequence of interest in a plant cell, which does not have the above-mentioned shortcomings and notably does not have the size limitation of the sequence of interest.

It is another object of the invention to provide a new process which allows amplification or expression of more than one nucleic acid sequences of interest in a plant cell.

Further it is an object of the invention to provide a process of amplification or expression of nucleic acid sequence(s) of interest in a plant cell, which is of improved ecological and biological safety.

Here, we describe a system that is devoid of the above limitations: it has no detectable limit on the size of DNA to be expressed, it allows expressing multiple genes in the same cell and plant and it possesses high built-in biosafety parameters.

SUMMARY OF THE INVENTION

This invention provides a process of causing amplification and/or expression of one or more nucleic acid sequences of interest in a plant, plant tissue, plant cell or cell culture, characterized in that a plant cell is provided with at least one precursor vector designed for undergoing processing in said cell, whereby due to said processing said plant cell is endowed with at least one replicon which provides for said amplification and/or expression, whereby said at least one replicon is preferably structurally related to each of said at least one precursor vectors owing to said processing.

This invention further provides a process of causing amplification and/or expression of one or more nucleic acid sequences of interest in a plant, plant tissue, plant cell or cell culture, characterized in that a plant cell is provided with at least one precursor vector designed for undergoing processing in said cell, whereby due to said processing said plant cell is endowed with at least two replicons which
(a) are structurally related to each other owing to said processing;
(b) are functionally distinct from each other; and
(c) provide for said amplification and/or expression.

Further, the invention provides a process of causing amplification and/or expression of one or more nucleic acid sequences of interest in a plant, plant tissue, plant cell or cell culture, characterized in that a plant cell is provided with at least two precursor vectors designed for undergoing processing in said cell preferably by site-specific recombination, whereby due to said processing said plant cell is endowed with at least one replicon which provides for said amplification and/or expression. Preferably, said at least one replicon is structurally related to each of said at least two precursor vectors owing to said processing.

This invention further describes a process for the production of a biochemical product, a process for gene function determination, and a process for artificial or directed evolution, whereby each of these processes comprises one of the above processes of causing amplification and/or expression.

Moreover, vectors or precursor vectors and viral material for this process are provided and viral material, replicons and plant material obtained or obtainable by performing this process. Viral material comprises nucleic acids capable of replicating in a plant cell. It comprises infectious DNA or RNA. Viral material may be naked or coated with a coat protein.

Further, a kit-of-parts comprising (i) plant cells, seeds or plants and (ii) the above vectors, precursor vectors, viral material, or replicons are provided. A further kit-of-parts is provided comprising (i) plant cells, seeds or plants and (ii) *Agrobacterium* cells containing the above vectors, precursor vectors, viral material, or replicons.

The process of the invention causes amplification and/or expression of one or more nucleic acid sequences of interest in a plant cell. Amplification refers to the production of DNA or RNA (e.g. for anti-sense technology). Expression refers to the formation of a polypeptide or protein. In both cases, the ultimate goal may be a biochemical product the production of which may require amplification of said DNA or RNA and/or expression of a polypeptide or protein.

The process of the invention may be carried out in a plant, plant tissue, plant cell or cell culture. It is preferred to carry out said process in plant cells. Most preferably, said process is carried out in a plant.

According to the invention, providing a plant cell with a precursor vector may comprise viral transfection, *Agrobacterium*-mediated delivery, non-biological delivery, or conversion of a replicon pre-precursor DNA that was pre-integrated into a plant nuclear DNA to form a precursor vector or vectors. However, said providing a plant cell with a precursor vector may further comprise, in addition to transfection or transformation, cellular action, e.g. in the case of RNA virus-based precursor vectors, a primary transformed or transfected DNA may require transcription in order to produce the RNA precursor vector in the cell. In the case of *Agrobacterium*-mediated delivery, the precursor vector may have to be excised or transcribed from T-DNA delivered by *Agrobacterium*.

A replicon is a DNA or RNA molecule capable of autonomous replication in a cell of said plant. Examples include: bacterial and yeast plasmids, plastids and mitochondrial DNA, DNA and RNA viruses, viroids, phages. A replicon has to have an origin of replication. The origin of replication may be recognized by a DNA or RNA polymerase of the host plant cell, depending on whether the replicon is a DNA or an RNA replicon, or by a heterologous polymerase e.g. of viral origin. In this case, the plant cell has to be provided with said heterologous polymerase e.g. by one of said replicons. The autonomous replication of the replicons in the plant cell has presumably the effect that their concentration is increased, which may increase the expression level of the sequences of interest and support spread from cell-to-cell and throughout the plant. Preferably, replicons have an increased infectivity and ability to spread compared to precursor vectors.

Said at least one or said at least two replicons may retain additional viral capabilities such as viral particle assembly, infectivity, suppression of gene silencing, reverse transcription, integration into the host chromosome, cell to cell movement, or long distance movement. One of said replicons may essentially be a helper type virus which provides in trans functions necessary for replication of another replicon or replicons. Further, one of said replicons may essentially be a wild-type retrovirus or retrotransposon which provides in trans functions necessary for replication, reverse transcription, integration into a host chromosome of another replicon or replicons.

Said at least one or said at least two replicons provide, preferably together, for the amplification and/or expression of said nucleic acid sequences of interest. If one sequence of interest is amplified or expressed from one of said replicons another replicon may be required e.g. for a function necessary for the replication of said replicons or for spreading of at least one replicon to neighboring cells if said process is performed in cell culture or in a plant. In this case, the replicons cooperate functionally with each other.

If more than one sequence of interest is to be amplified or expressed, each sequence may preferably be expressed from one replicon, whereby the replicons provide (together) for said amplification or expression. Also in this case, the replicons preferably cooperate functionally with each other. As an example, a function for replication or spreading of said replicons may be expressed from one or some of said replicons which amplify or express said sequences of interest or from an additional replicon. Without functional cooperation, the amplification or expression level would be much lower or be limited to the cell(s) provided with said precursor vector(s), if amplification or expression is desired in plant cells or a plant.

Said at least one or said at least two replicons are functionally distinct from each other in that they provide different functions for amplification and/or expression of said sequence(s) of interest. Examples for such functions include, in addition to coding of said nucleic acid sequence(s) of interest, the expression of products necessary for replicating the replicons, expression of factors or products (preferably enzymes) which facilitate the processing of the precursor vector(s) to give said replicons, expression of products necessary for cell to cell or long distance or plant to plant movement of said replicons (e.g. movement protein or coat protein) etc. These products may function in trans or in cis. Functional distinctness does not include random mutations in the replicons which may occur in the course of the processing in the plant cell.

Owing to said processing, said at least replicons are structurally related to each other in that they share sequence portions with each other. The type of the relatedness depends on the type of processing (modification process). If one replicon is produced in said process, said replicon is structurally related to said at least one or to each of said at least two precursor vectors owing to said processing.

The precursor vectors of the invention undergo processing in the plant cell by one of the following DNA or RNA modification processes, which endows the plant cell with the replicon or replicons according to the invention. The processing in the plant cell may involve DNA modification such as DNA recombination, insertion or excision etc. Alternatively, it may involve RNA modification such as RNA splicing, ligation or recombination etc. Within this invention, said processing does not include transcription. The precursor vector may itself be a DNA or RNA molecule capable of autonomous replication in a cell of said plant.

The precursor vector(s) of this invention are preferably of plant viral origin, more preferably of an RNA virus or DNA virus origin. Examples of specific viruses are given below. Precursor vectors may be capable of autonomous replication in the plant cell as are replicons.

The plant cell may be provided with one or more precursor vectors. If the cell is provided with only one precursor vector, this precursor endows the plant cell with at least two replicons. If the cell is provided with two or more precursor vectors, the cell is preferably endowed with said at least one or said at least two replicons by a processing which involves interaction between said precursor vectors, e.g. recombination. Providing the plant cell with two or more precursor vectors greatly increases the possibilities for generating the replicon or replicons of the invention. Several different DNA or RNA modifications may occur in the plant cell depending on the design of the precursor vectors.

The process according of the invention is based on the use of a wild-type plant cell(s) or on a plant cell(s) that is (are) genetically engineered so as to provide functions necessary for said processing, or to provide in trans one or more functions necessary for infectivity, replicon replication, virus particle assembly, suppression of gene silencing by the host, integration into a host chromosome, reverse transcription, cell to cell or long distance movement of said resultant replicons. Said genetic engineering of said plant cell is done by transient expression, virus- or *Agrobacterium*-mediated transfection, stable integration into genomes of nuclei or organelles or into autonomously replicating plasmids of said plant cell. The plant cells and plants for the process of this invention are preferably higher plants or cells thereof. Crop plants are particularly preferred.

The process of causing amplification or expression according to the invention features several important advantages over the prior art. The size of the nucleic acid sequence(s) of interest to be amplified or expressed is far less limited than in the prior art, since functions necessary for amplification or expression are shared by at least two replicons, whereby the replicons are smaller than a prior art vector would be. Consequently, amplification or expression is more efficient.

Furthermore, the process of the invention allows the amplification and/or expression of more than one nucleic acid sequence of interest. Examples are provided for the expression of two genes of interest. However, the expression of three, four or even more nucleic acid sequence of interest is feasible within this invention. This allows the expression of a whole biochemical pathway or cascade or of a multi-subunit protein. Each sequence of interest may preferably be expressed from one replicon. Additional function(s) for efficient performance of the process like those listed below may be located on an additional replicon. Alternatively, a replicon may encode more than one of these functions.

A third important advantage of the invention is that there are several possibilities of improving the biological safety over prior art processes. In embodiments wherein more than one precursor vector is employed, the process is only functional when all precursors get into the plant cell. Alternatively, the processing in the cell to generate said at least one or said at least two replicons may be dependent on an additional component e.g. an enzyme which catalyses said processing. Then the system is only functional if the additional component is delivered into the cell or if a transgenic cell expressing said component is used. In one embodiment, the replicon which expresses a sequence of interest can spread throughout the plant from the primary infected cell, but spreading to other plants is not possible.

Examples for nucleic acid sequences of interest include coding sequences or parts thereof, or any genetic element. Herein, a genetic element is any DNA or RNA element that has a distinct genetic function other than coding for a structural part of a gene. Examples include: transcriptional enhancer, promoters, translational enhancers, recombination sites, transcriptional termination sequences, internal ribosome entry sites (IRESes), restriction sites. A preferred genetic element is a tobamoviral $IRES_{mp}75$ used as translational enhancer operably linked to a heterologous nucleic acid sequence encoding a protein of interst.

In a preferred embodiment of the invention, said plant cell is endowed with at least one (type of) replicon. Said one replicon is preferably formed by site-specific recombination between at least two precursor vectors. Said site-specific recombination preferably takes place on DNA level. Said one replicon may therefore be DNA. Alternatively, said one replicon may be RNA formed by transcription following said site-specific recombination. In this embodiment, said precursor vectors are preferably not capable of autonomous replication in said plant cell. This embodiment is particularly preferred from the point of view of biological safety.

In another preferred embodiment of the invention, a plant cell is provided with the cDNA of a precursor vector (FIGS. 2 and 4). After transcription which produces the precursor vector, processing in the cell by splicing endows the cell with an RNA virus-based replicon from which a sequence of interest can be amplified or expressed. Since splicing is slow and/or does not happen in all the precursor vector molecules in the cell, unspliced precursor molecules will remain in the cell. For the purpose of this invention, these remaining unspliced precursor vectors are replicons as well provided they are capable of autonomous replication. In this invention, they are used for the expression of (a) function(s) necessary for amplification or expression of said sequence of interest, e.g. a function for spreading of the replicon(s) to neighbor cells.

In another preferred embodiment, a set of replicons of the type $AB_1, AB_2, \ldots, AB_n$ or of the type $B_1A, B_2A, \ldots, B_nA$ are generated in a cell by site-specific recombination of a primary precursor vector (A) with a set of at least two secondary precursor vectors $(B_1, B_2, \ldots, B_n)$ wherein n is an integer of $\geq 2$. In the embodiment shown in FIG. 8, precursor vectors (secondary vectors) containing a sequence to be expressed or amplified are recombined with another precursor vector (primary precursor vector) to form replicons of the type $AB_1, AB_2$ and $AB_3$, from which these sequences can be amplified or expressed. At least three precursor vectors are needed to endow the cell with at least two replicons. Preferably, functions for spreading the replicons are expressed from one or more of said replicons.

For performing the processes of the invention, precursor vectors may directly be used for transforming or transfecting a plant or plant cell. This is particularly true for DNA virus-based replicons. For RNA virus-based replicons, DNA vectors used for transformation or transfection require transcription for producing the precursor vectors inside the cell.

The processes of the invention may be used for generating high amounts of one or more nucleic acid sequences in a plant, plant tissue, plant cell or cell culture in an environmentally safe way. Notably, said processes may be used for generating high amounts of said at least one or said at least two replicons. Said replicon(s) may be purified or enriched from the plant material. Said replicon(s) may be vectors or viral material that may be used, optionally after enrichment or purification, for transforming or transfecting a further plant, plant tissue, plant cells or cell culture. In this embodiment, the processes of the invention may be biologically safe processes of producing infectious viral material or vectors for transforming or transfecting plants on a large scale like on an agricultural or farming scale. Said infectious viral material or said vectors may be packaged or coated viral material. The protein material necessary for packaging said viral material may be expressed from said replicon(s).

The processes of the invention may be used for the production of a biochemical product. Said biochemical product is preferably a protein, more preferably a pharmaceutical protein. Said pharmaceutical protein may be a functional antibody.

The processes of the invention may further be used for gene function determination, notably for rapid gene function determination or for functional genomics analysis.

The processes of the invention may further be used for for artificial or directed evolution, notably for artificial or directed gene evolution or for artificial or directed evolution of genetic elements.

DETAILED DESCRIPTION OF THE INVENTION

Figure 1:
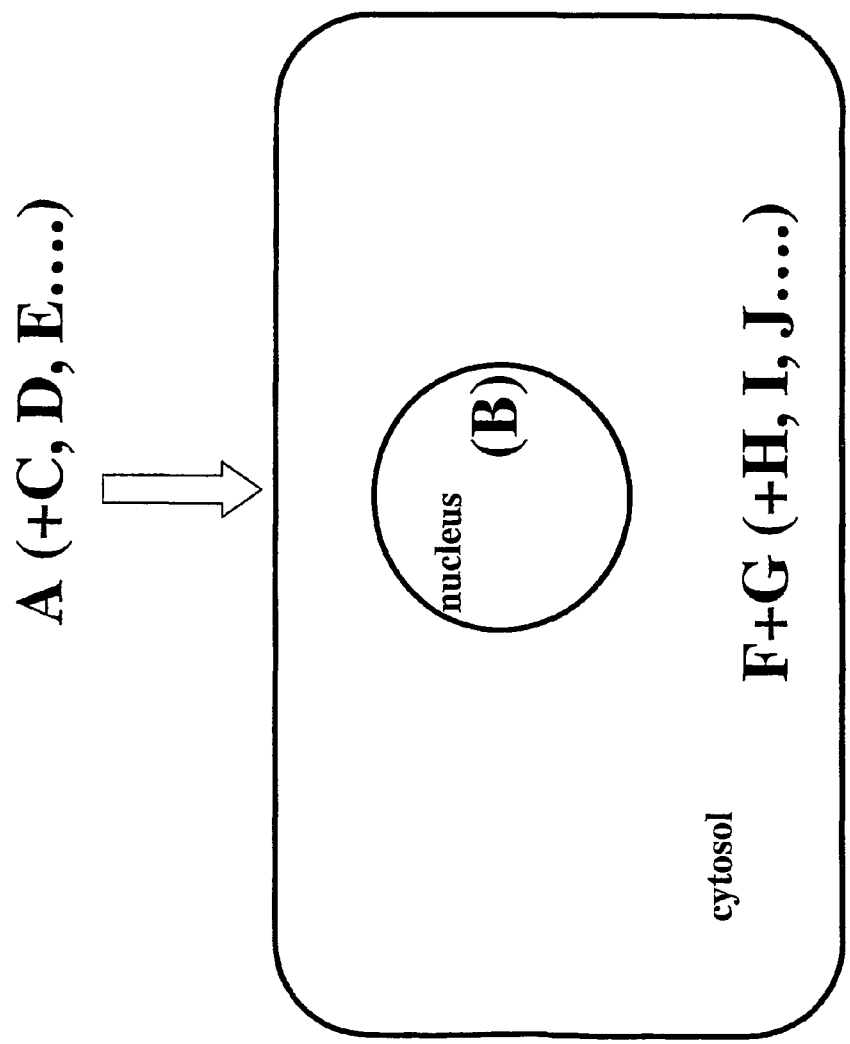
FIG. 1 depicts the general principle of generating replicons from precursor vectors in planta.

In the present invention an approach for amplification and/or expression of one or more nucleic acid sequences of interest is described which has all the potentials of viral vector systems, yet lacks their disadvantages such as limited capacity. Further, it offers better biosafety characteristics. Viruses belonging to different taxonomic groups can be used for the construction of virus-based vectors according to the principles of the present invention. This is true for both RNA- and DNA-containing viruses, examples for which are given in the following (throughout this document, each type species' name is preceded by the name of the order, family and genus it belongs to. Names of orders, families and genera are in italic script, if they are approved by the ICTV. Taxa names in quotes (and not in italic script) indicate that this taxon does not have an ICTV international approved name. Species (vernacular) names are given in regular script. Viruses with no formal assignment to genus or family are indicated):

DNA Viruses:

Circular dsDNA Viruses: Family: Caulimoviridae, Genus: *Badnavirus*, Type species: commelina yellow mottle virus, Genus: *Caulimovirus*, Type species: cauliflower mosaic virus, Genus "SbCMV-like viruses", Type species: Soybean chloroticmottle virus, Genus "CsVMV-like viruses", Type species: Cassava vein mosaicvirus, Genus "RTBV-like viruses", Type species: Rice tungro bacilliformvirus, Genus: "Petunia vein clearing-like viruses", Type species: Petunia vein clearing virus;

Circular ssDNA Viruses: Family: Geminiviridae, Genus: *Mastrevirus* (Subgroup I Geminivirus), Type species: maize streak virus, Genus: *Curtovirus* (Subgroup II Geminivirus), Type species: beet curly top virus, Genus: *Begomovirus* (Subgroup III Geminivirus), Type species: bean golden mosaic virus;

RNA Viruses:

ssRNA Viruses: Family: Bromoviridae, Genus: *Alfamovirus*, Type species: alfalfa mosaic virus, Genus: *Ilarvirus*, Type species: tobacco streak virus, Genus: *Bromovirus*, Type species: brome mosaic virus, Genus: *Cucumovirus*, Type species: cucumber mosaic virus;

Family: Closteroviridae, Genus: *Closterovirus*, Type species: beet yellows virus, Genus: *Crinivirus*, Type species: Lettuce infectious yellows virus, Family: Comoviridae, Genus: *Comovirus*, Type species: cowpea mosaic virus, Genus: *Fabavirus*, Type species: broad bean wilt virus 1, Genus: *Nepovirus*, Type species: tobacco ringspot virus;

Family: Potyviridae, Genus: *Potyvirus*, Type species: potato virus Y, Genus: *Rymovirus,* Type species: ryegrass mosaic virus, Genus: *Bymovirus*, Type species: barley yellow mosaic virus;

Family: Sequiviridae, Genus: *Sequivirus*, Type species: parsnip yellow fleck virus, Genus: *Waikavirus*, Type species: rice tungro spherical virus; Family: Tombusviridae, Genus: *Carmovirus*, Type species: carnation mottle virus, Genus: *Dianthovirus*, Type species: carnation ringspot virus, Genus: *Machlomovirus*, Type species: maize chlorotic mottle virus, Genus: *Necrovirus*, Type species: tobacco necrosis virus, Genus: *Tombusvirus*, Type species: tomato bushy stunt virus, Unassigned Genera of ssRNA viruses, Genus: *Capillovirus*, Type species: apple stem grooving virus;

Genus: *Carlavirus*, Type species: carnation latent virus; Genus: *Enamovirus*, Type species: pea enation mosaic virus, Genus: *Furovirus*, Type species: soil-borne wheat mosaic virus, Genus: *Hordeivirus*, Type species: barley stripe mosaic virus, Genus: *Idaeovirus*, Type species: raspberry bushy dwarf virus;

Genus: *Luteovirus*, Type species: barley yellow dwarf virus; Genus: *Marafivirus*, Type species: maize rayado fino virus; Genus: *Potexvirus*, Type species: potato virus X; Genus: *Sobemovirus*, Type species: Southern bean mosaic virus, Genus: *Tenuivirus*, Type species: rice stripe virus, Genus: *Tobamovirus*, Type species: tobacco mosaic virus, Genus: *Tobravirus*, Type species: tobacco rattle virus, Genus: *Trichovirus*, Type species: apple chlorotic leaf spot virus; Genus: *Tymovirus*, Type species: turnip yellow mosaic virus; Genus: *Umbravirus*, Type species: carrot mottle virus; Negative ssRNA Viruses: Order: Mononegavirales, Family: Rhabdoviridae, Genus: *Cytorhabdovi-* rus, Type Species: lettuce necrotic yellows virus, Genus: *Nucleorhabdovirus,* Type species: potato yellow dwarf virus;

Negative ssRNA Viruses: Family: Bunyaviridae, Genus: *Tospovirus,* Type species: tomato spotted wilt virus;

dsRNA Viruses: Family: Partitiviridae, Genus: *Alphacryptovirus,* Type species: white clover cryptic virus 1, Genus: *Betacryptovirus,* Type species: white clover cryptic virus 2, Family: Reoviridae, Genus: *Fijvirus,* Type species: Fiji disease virus, Genus: *Phytoreovirus,* Type species: wound tumor virus, Genus: *Oryzavirus,* Type species: rice ragged stunt virus; Unassigned Viruses: Genome ssDNA: Species: banana bunchy top virus, Species coconut foliar decay virus, Species: subterranean clover stunt virus, Genome: dsDNA, Species: cucumber vein yellowing virus; Genome: dsRNA, Species: tobacco stunt virus, Genome: ssRNA, Species Garlic viruses A,B,C,D, Species grapevine fleck virus, Species maize white line mosaic virus, Species olive latent virus 2, Species: ourmia melon virus, Species Pelargonium zonate spot virus;

Satellites and Viroids: Satellites: ssRNA Satellite Viruses: Subgroup 2 Satellite Viruses, Type species: tobacco necrosis satellite, Satellite RNA, Subgroup 2 B Type mRNA Satellites, Subgroup 3C Type linear RNA Satellites, Subgroup 4 D Type circular RNA Satellites, Viroids, Type species: potato spindle tuber viroid.

Mostly, vectors of plant viral origin are used as plasmids capable of autonomous replication in plants (replicons). However the principles necessary for engineering such plasmids using non-viral elements are known. For example, many putative origins of replication from plant cells have been described (Berlani et al., 1988, *Plant Mol. Biol.,* 11, 161-162; Hernandes et al., 1988, *Plant Mol. Biol.,* 10, 413-422; Berlani et al., 1988, *Plant Mol. Biol.,* 11, 173-182; Eckdahl et al., 1989, *Plant Mol. Biol.,* 12, 507-516). It has been shown that the autonomously replicating sequences (ARS elements) from genomes of higher plants have structural and sequence features in common with ARS elements from yeast and higher animals (Eckdahl et al., 1989, *Plant Mol. Biol,* 12, 507-516). Plant ARS elements are capable of conferring autonomous replicating ability to plasmids in *Saccharomyces cerevisiae.* Studies of maize nuclear DNA sequences capable of promoting autonomous replication of plasmids in yeast showed that they represent two families of highly repeated sequences within the maize genome. Those sequences have a characteristic genomic hybridization pattern. Typically there was only one copy of an ARS-homologous sequence on each 12-15 kb of genomic fragment (Berlani et al.,1988, *Plant Mol. Biol.,* 11:161-162). Another source of replicons of plant origin are plant ribosomal DNA spacer elements that can stimulate the amplification and expression of heterologous genes in plants (Borisjuk et al., 2000, *Nature Biotech.,* 18, 1303-1306).

Therefore, a replicon or precursor vector contemplated in this invention is not necessarily derived from a plant virus. Plant DNA viruses provide an easy way of engineering replicons (vectors) that could be especially useful for targeted DNA transformation, but vectors made entirely or partially of elements from plant RNA viruses or even non-plant viruses are possible. Plant virus-based replicons are evidently advantageous. Such replicons, in addition to replication, may provide additional useful functions e.g. for cell to cell and long distance movement. Further, they can frequently be removed more easily from the plant cell aposteriori by using known methods of virus eradication from infected plants.

The general principle of the invention is shown in FIG. 1. In the simplest example, one type of precursor vector (pro-vector) (A) is delivered into the plant cell where, upon its processing in said cell, it yields at least one or at least two structurally related and functionally distinct replicons (F and G) which are able to provide amplification and/or expression of the sequences of interest. More than one precursor vector can be introduced into the plant cell [A(+C,D,E . . . )]. Optionally, said plant cell can be transgenic and contain another additional component (B) required for the processing of the precursor vector and/or expression, replication, cell-to-cell or systemic movement.

Figure 4:
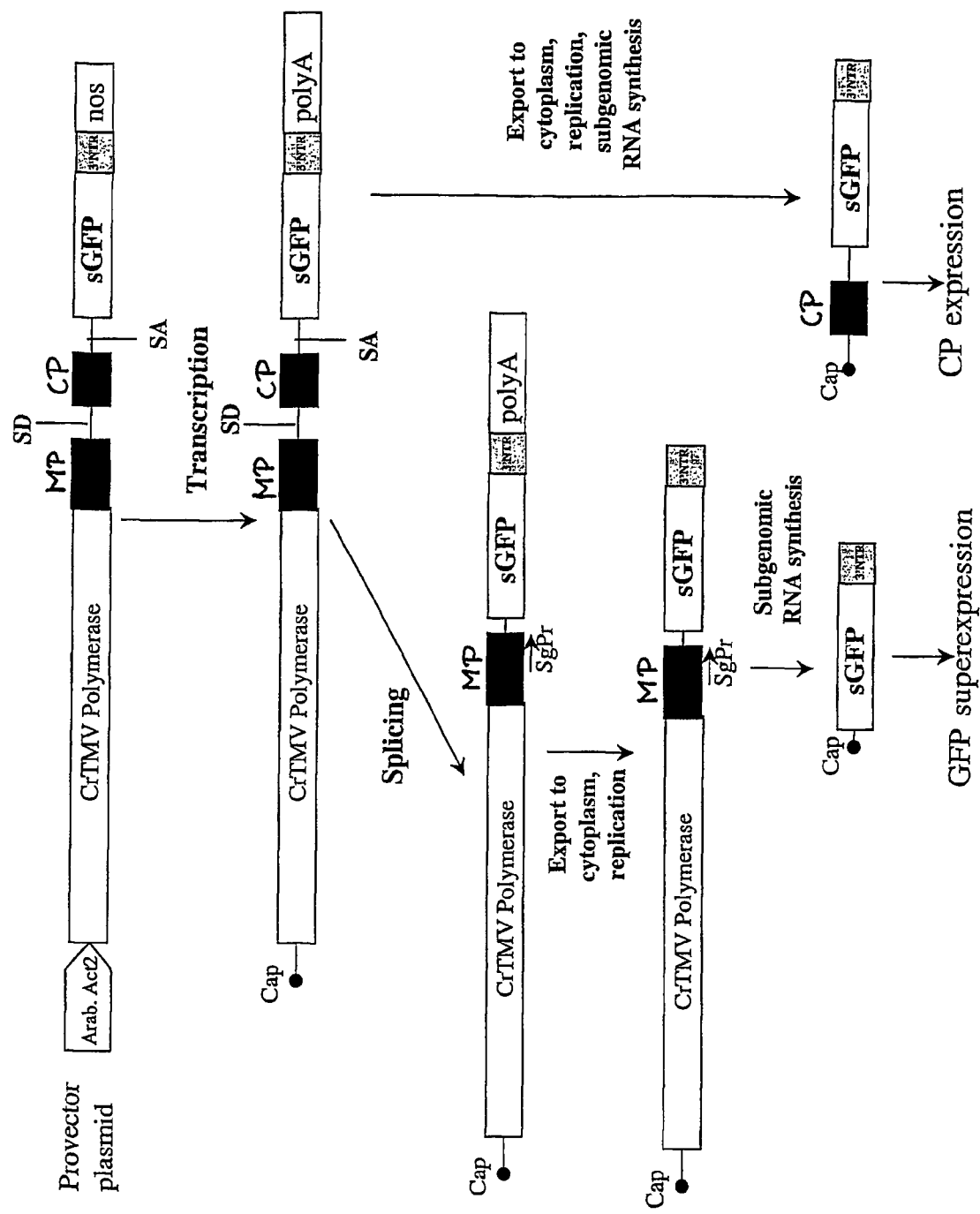
FIG. 4 depicts the general scheme of expression of two genes (CP and GFP) using a CrTMV-based spliceable precursor vector (provector).

In one embodiment of the invention, we describe a pro-vector (precursor vector) system that is based on the splicing of the pro-vector RNA in the plant nucleus. This system comprises a DNA molecule of the pro-vector containing parts of plant virus genome cDNA, gene(s) of interest and splicing-sites functional in the plant cell (see for example FIG. 2 or 4). After transcription in the transfected plant cell, the primary RNA product (pro-vector or precursor vector) can be processed by splicing. Due to the design of the pro-vector (precursor vector), the gene of interest (e.g. GFP) substitutes one of the viral genes (e.g. CP) in this spliced form. This allows the gene of interest (GFP) to be expressed via the normal viral pathway instead of substituted viral protein. However, since splicing cannot proceed with 100% efficiency, a fraction of the primary transcript remains unspliced and is exported from the nucleus as is the spliced form. As a result, two types of self-replicating viral vector RNAs (replicons) appear in the cytoplasm of the transfected plant cell. This leads to the expression of both GFP and CP from replicons generated using one precursor vector. It must be mentioned that, in the exemplified case, the level of GFP expression is likely much higher than that of CP. It was shown for tobamoviruses that the amount of viral protein produced during infection depends on the distance between gene encoding the protein and 3'-terminus of the virus. Since GFP is expressed from the spliced form of RNA, the corresponding subgenomic RNA is significantly shorter than the RNA from which CP is expressed (FIG. 4; sGFP stands for a synthetic or engineered GFP).

As an exemplification of this embodiment we constructed two pro-vectors (precursor vectors) based on two well-known plant viruses: potato virus X (PVX) and crucifer infecting tobamovirus (CrTMV). In both cases, the CP gene of the viruses was flanked with donor (upstream) and acceptor (downstream) splicing sites (SA and SD, respectively). GFP was cloned downstream of the acceptor site to be expressed only in the spliced transcript. The physiological roles of CP in PVX and CrTMV are different. In the case of PVX, CP is required for cell-to-cell movement of the virus. In CrTMV, CP participates mainly in long-distance spread of the virus (systemic infection) and is not crucial for infection of neighbor cells. These examples provide two different patterns of reporter gene (GFP) expression. In the case of the PVX-based system, viral spread is stalled in primary transfected cells until the required amount of CP is expressed from a less efficient replicon that was formed from unspliced RNA. This leads to super-production of much more rapidly synthesized GFP in the same cell. Finally, the necessary amount of CP accumulates and both replicons penetrate neighbor cells where the process repeats. On the contrary, in the case of the CrTMV-based pro-vector, viral spread is not limited to cell-to-cell movement. Both forms of the vector act independently, which leads to faster growth of the infected area.

Although specific examples describing RNA modification as a mechanism for generating replicons according to the invention are based on RNA splicing, other RNA modification mechanisms may be used for the process of this invention as well. These include inter alia modifications as RNA ligation or RNA recombination. Ligation of different RNA molecules by enzymes such as RNA ligase allows to produce a plurality of different RNA replicons within a cell based on the internal enzymatic activity of plant cells or based on the expression of well known ligases such as T4 RNA ligase (Nishigaki et al., 1998, *Mol. Divers.*, 4, 187-190) or mitochondrial RNA ligase from *Leishmania* (Blanc et al., 1999, *J. Biol. Chem.*, 274, 24289-24296). RNA-RNA recombination is a well researched phenomenon. It readily occurs in a plant host between viral RNA molecules with a certain degree of homology (Allison et al., 1990, *Proc. Natl. Acad. Sci.* 87, 1820-1824; Rao et al., 1990, *J. Gen. Virol.*, 71, 1403-1407; U.S. Pat. No. 5,877,401).

In another embodiment, the precursor vectors are processed by site-specific DNA recombination producing a replicon or partially different replicons or assembling one viral replicon in vivo. In this case, molecular rearrangements proceed on the DNA level. Several molecules (pro-vectors) are shuffled by means of recombination to produce one or several vector molecules (replicons). The first DNA-component of the system may contain a plant promoter (*Arabidopsis* Actin 2) fused to the main part of CrTMV genome—the polymerase gene plus the MP gene followed by a specific recombination site. Secondary components are plasmid DNAs comprising the same recombination site followed by a gene(s) of interest (any reporter gene) or viral CP gene. The 3'-UTR of CrTMV should be cloned downstream of the gene of interest. The last component of the system may be Cre-recombinase or integrase expressing DNA. These enzymes promote reorganization of pro-vector components into active vector molecules (replicons). It must be stressed that none of the pro-vector components is infectious alone, which is important in terms of the biological safety of the system.

Figure 8:
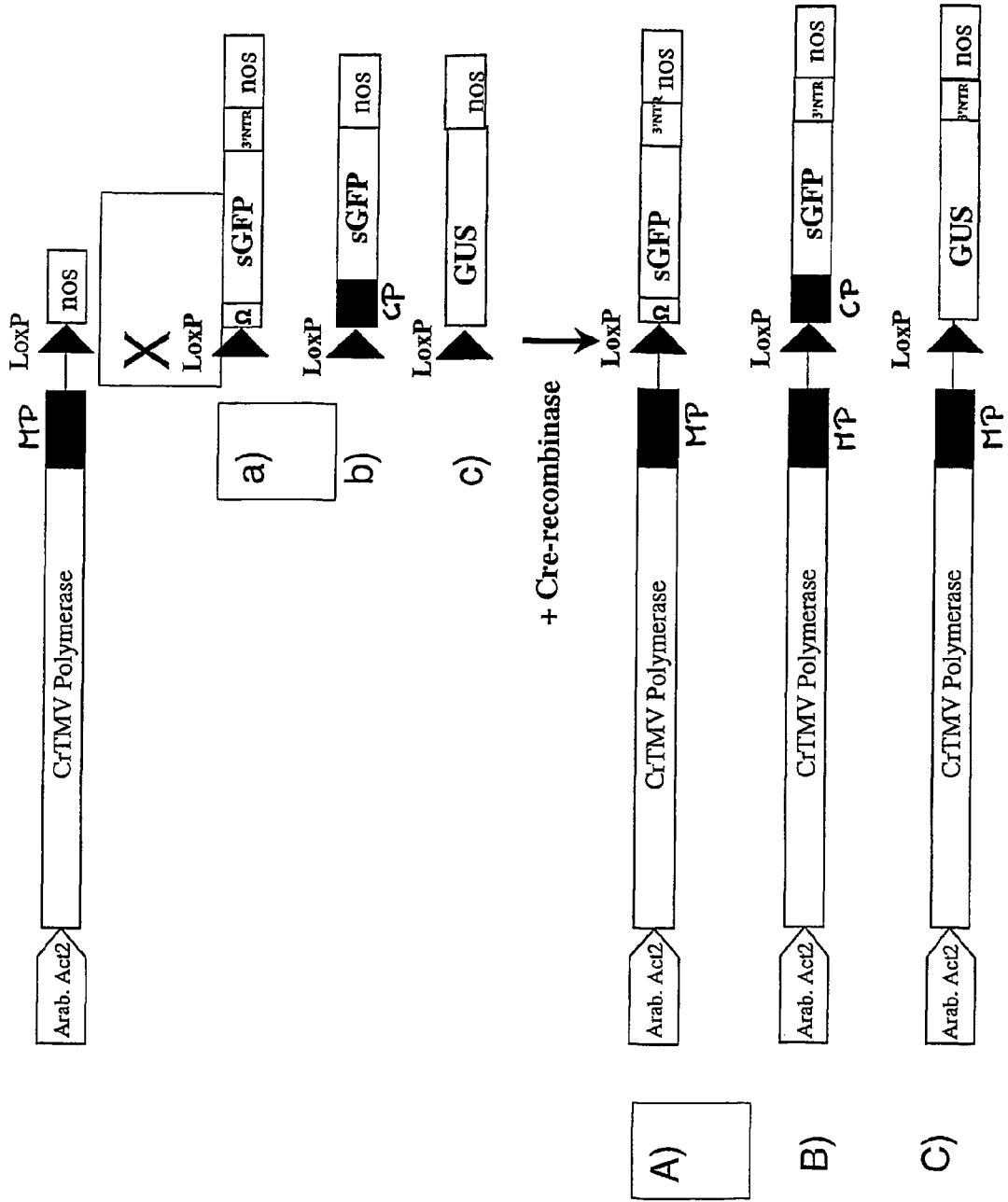
FIG. 8 depicts the general scheme of expression of several genes via CrTMV-based precursor vectors (a-c and vector shown at the top) and generation of replicons (A-C) by site-specific recombination at LoxP-sites catalyzed by the enzyme Cre recombinase.

After providing a plant cell with all the components of the described multi-component system, recombination occurs and one or several replicons can be formed (see FIGS. 8A,B, C). These rearranged DNA molecules can be transcribed (since they carry *Arabidopsis* Actin 2 promoter) in the nucleus and exported to the cytoplasm. Finally, like in the case involving RNA splicing, several replicating vector RNAs appear in the cytoplasm of the transfected cell. In this embodiment, we describe the system where all of these vectors contain a functional MP gene and a gene positioned downstream. This allows each vector RNA to express both a functional MP gene and a gene positioned downstream and to penetrate into neighbor cells. One has to state that other combinations are also possible and are contemplated as being within the scope of this invention.

Two different approaches of recombinase delivery are exemplified in the invention. The recombinase may be delivered into the cell in a process of co-bombardment or by *Agrobacterium*-mediated transient expression together with other DNA-components of the system. As another approach, a transgenic plant expressing cre-recombinase has been obtained. This reduces the number of components the cell has to be provided with and as a result raises the overall efficiency of the system. Additionally, this further improves the safety of the process as it cannot occur outside of a plant that was genetically manipulated to support the process.

During the cloning of pro-vector components, a LoxP recombination site was cloned upstream of the gene of interest. A LoxP site contains two small inverted repeats spaced by several nucleotides and it forms stem-and-loop structure in RNA. The stem contains only 4 GC pairs so it is not very stable. However, this stem can reduce the efficiency of translation of a downstream gene. To solve this problem, any translational enhancer can be cloned between LoxP and the gene of interest. In the examples with Cre recombinase we used an omega leader of TMV U1. However any other translation-enhancing sequence can be used (e.g. $IRES_{mp}75$ from CrTMV or TMV U1) as well as plant IRESes. $IRES_{mp}75$ elements may preferably be used as translational enhancers as in the examples with integrase of phage PhiC31. In this case, in a set of provectors the LoxP recombination sites were replaced by att-sites (attachment-sites) from the *Streptomyces* phage PhiC31 (Thorpe & Smith, 1998, *Proc. Natl. Acad. Sci.*, 95, 5505-5510; Groth et al., 2000, *Proc. Natl. Acad. Sci.*, 97, 5995-6000) which are the target sequences for the recombination enzyme integrase. Two different att-sites were cloned into the provectors: Whereas attP was inserted in the vectors of the type polymerase-MP-LoxP, an attB-recombination site was cloned into the provectors, which carry the gene of interest followed by a 3'NTR sequence and a nosterminator. Similar to the Cre system, the att-recombination-sites limit the efficiency of translation of a gene, which is located downstream. Hence, also in this system translational enhancer sequences were cloned between the attB-sites and the genes of interest. It was shown that $IRES_{mp75}$ sequences have comparable or even better effect as translational enhancers in comparison with the omega leader of TMV U1.

Suitable recombinases/recombination site systems include inter alia the Cre-Lox system from bacteriophage P1 (Austin et al., 1981, *Cell*, 25, 729-736), the FIp-Frt system from *Saccharomyces cerevisiae* (Broach et al., 1982, *Cell*, 29, 227-234), the R-Rs system from *Zygosaccharomyces rouxii* (Araki et al., 1985, *J. Mol. Biol.*, 182, 191-203), the integrase from the *Streptomyces* phage PhiC31 (Thorpe & Smith, 1998, *Proc. Natl. Acad. Sci.*, 95, 5505-5510; Groth et al., 2000, *Proc. Natl. Acad. Sci.*, 97, 5995-6000), and resolvases. In addition, other methods of DNA rearrangement are contemplated to be within the scope of the present invention. Other DNA modification enzyme systems can all be used to generate related but functionally distinct replicons inside of a wild-type or a genetically engineered plant cell: restriction endonuclease, transposase, general or specific recombinase, etc.

Different methods may be used for providing a plant cell with precursor vectors. DNA may be transformed into plant cells by a Ti-plasmid vector carried by *Agrobacterium* (U.S. Pat. Nos. 5,591,616; 4,940,838; 5,464,763) or particle or microprojectile bombardment (U.S. Pat. No. 5,100,792; EP 00444882B1; EP 00434616B1). Other plant transformation methods can also be used like microinjection (WO 09209696; WO 09400583A1; EP 175966B1), electroporation (EP00564595B1; EP00290395B1; WO 08706614A1) or PEG-mediated transformation of protoplasts etc. The choice of the transformation method depends on the plant species to be transformed. For example, microprojectile bombardment is generally preferred for monocot transformation, while for dicots, *Agrobacterium*-mediated transformation gives better results in general. *Agrobacterium*-mediated delivery of precursor vectors is preferred.

Construction of plant viral vectors for the expression of non-viral genes in plants has been described in several papers (Dawson et al., 1989, *Virology*, 172, 285-293; Brisson et al., 1986, *Methods in Enzymology*, 118, 659; MacFarlane & Popovich, 2000, *Virology*, 267, 29-35; Gopinath et al., 2000, *Virology*, 267, 159-173; Voinnet et al., 1999, Proc. Natl. Acad. Sci. USA, 96, 14147-14152) and can be easily performed by those skilled in the art.

The current invention has a number of advantages compared to existing viral vector-based strategies to express foreign genes in plants.

Most importantly, the process can be used for the expression of more than one nucleic acid sequence of interest and can thus be used for the expression of multiple genes of a biochemical pathway or cascade. In this regard, the process of the invention is the only available method that can be effectively used for the expression of genes for the purpose of gene function determination or for the purpose of biochemical production.

Figure 13:
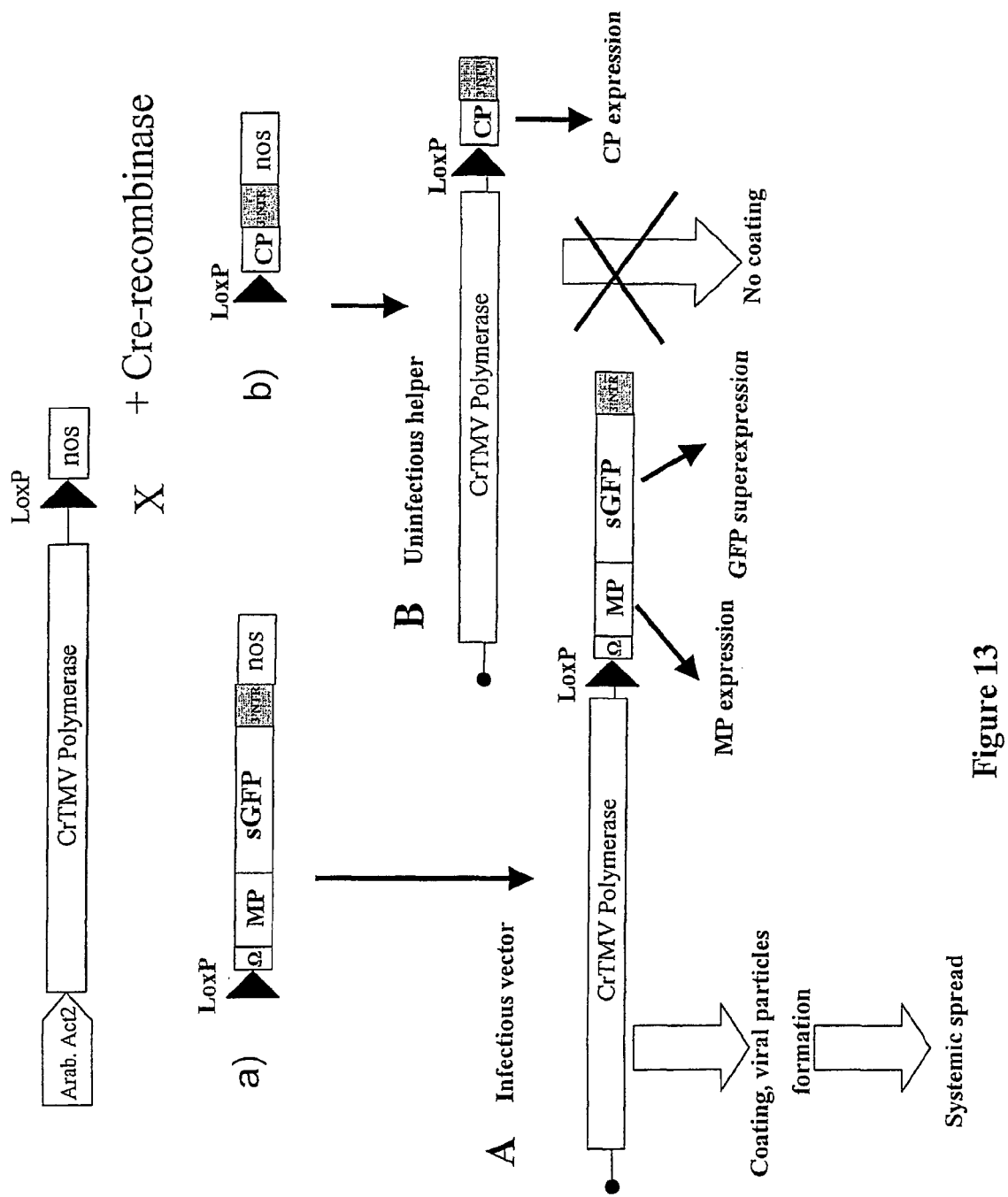
FIG. 13 depicts the principal scheme of transgene expression via a noncontagious viral vector.
Figure 14:
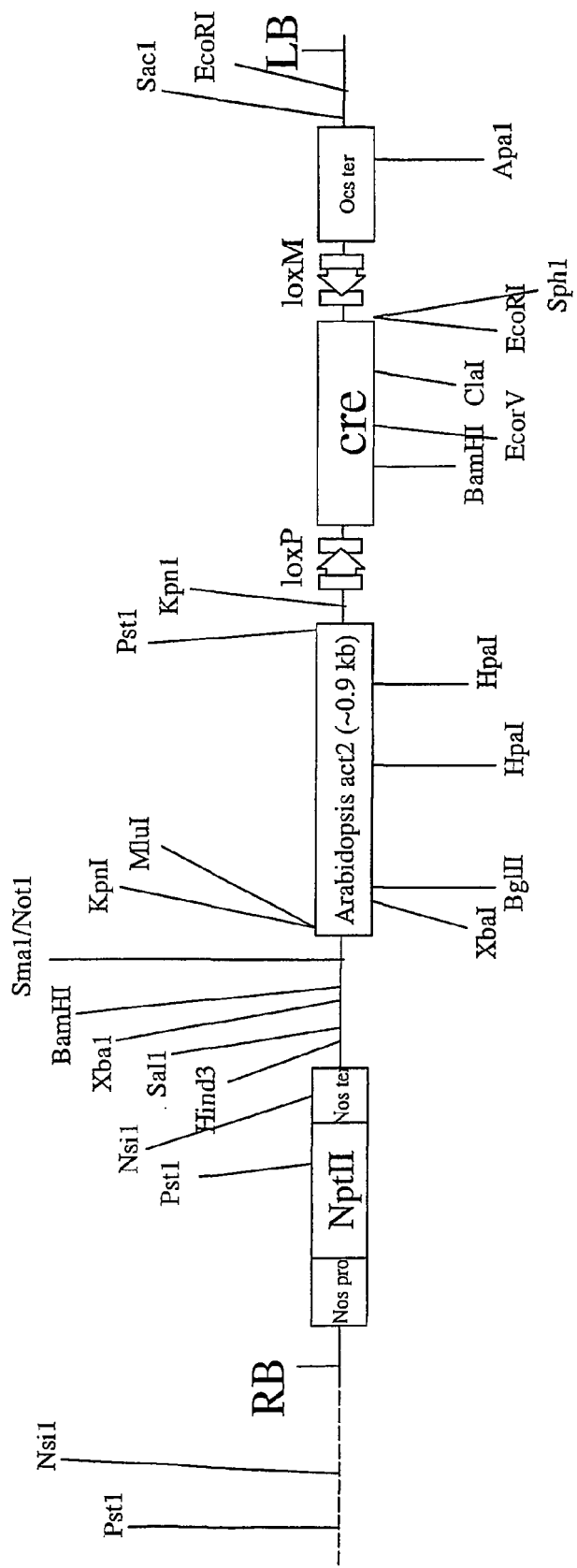
FIG. 14 depicts the structure of plasmid pIC1593 used to introduce a Cre recombinase gene into the genome of *N. benthamiana*.

The invention also opens up a wide range of opportunities for any kind of biological cascade construction. One example is presented in FIG. 13. This system utilizes recombination of 3 precursor vector components into 2 replicons. First, replicon A expresses MP and a gene of interest (GFP in the example). Due to the expression of the movement protein (MP), this vector is able to move from cell-to-cell in the inoculated leaf. However it cannot spread systemically in the infected plant and cannot be transmitted to other plants due to the absence of the coat protein (CP). In other words, this replicon is infectious only if it is artificially delivered into a plant cell. The second replicon B expresses only CP. Note that it is not able to form viral particles since its RNA lacks the origin of virus assembly (positioned inside the MP gene). However it does express CP in significant amounts.

The proposed process is inherently more safe as it is operable only in the presence of all the precursor vectors. If both of the replicons described above are present in the same cell, they complement each other and both components are able to move to neighbor cells. However only vector A can be coated with CP to form viral particles and therefore only this component will be exported from the infected leaf into the whole plant. If such viral particles penetrate uninfected leaves, they deliver only the infectious component A, but not B. This leads to the systemic spread of infection in the whole plant but the virus cannot infect other plants because viral particles can be formed only in primary inoculated leaves and these particles contain only one replicon component, which is not enough for systemic infection of another plant. This system represents a unique example of highly efficient expression of a transgene in the whole plant via a noncontagious viral vector.

Additionally, the process of assembly of one viral replicon from at least two replicon precursors through site-specific DNA recombination guaranties a higher level of safety in comparison with convenient viral vector being used for infecting plant cells. Said process of viral replicon assembly from at least two components requires the presence of said two components and a site-specific recombinase to be present in the same plant cell. Said recombinase can be delivered in cis together with one of said components. Preferably, the recombinase can be delivered separately. More preferably, the host plant can be engineered to expresses said recombinase. In the latter case, assembly of functional vector from provector elements will be restricted specifically to engineered host plant.

The described technology allows for higher efficiency of gene expression compared to conventional systems. This is achieved by reducing the size of the replicon or the replicons that express the gene. In our system, the size is significantly reduced compared to other viral vectors since the precursor vector can afford to express some viral gene(s) required for the function of the system from additional components or vectors (replicons) in trans. As mentioned above, the size of viral RNA does dramatically affect the level of transgene(s) expression.

Another technical advantage of the system is that its users do not have to clone anything into full-length cDNA copy of the virus This difficult and time-consuming process is avoided because one can use a pre-made construct (similar to pIC3461, FIG. 9) containing a promotor, a viral replicase gene and (optionally) a movement protein gene. This construct requires no further modification for any application. The only cloning a user has to perform is to fuse a gene of interest with some small additional sequences (recombination site, 3'-UTR of the virus and transcription terminator signal, wherein the total size is less than 1 kb) in any kind of high-copy plasmid. This advantage is especially important in case of genes which products are toxic for bacteria and require special handling during cloning, as well as for high throughput processes.

EXAMPLES

Example 1

Construction of Spliceable PVX-based Provector

Two 35-PVX based provectors have been constructed. Plasmid PVX-201 was used as a basic construct for cloning (Chapman S et al., 1992, Plant J 1992 July;2(4):549-57). This plasmid contains the full-length cDNA of the potato virus X (PVX) genome (Gene Bank Accession Numbers NC 001455; AF172259) fused to the $^{35}$S promoter and the nos terminator. The CP subgenomic promoter region is duplicated and a few cloning sites are inserted between the duplicated regions in PVX-201 (see FIG. 3).

Figure 3:
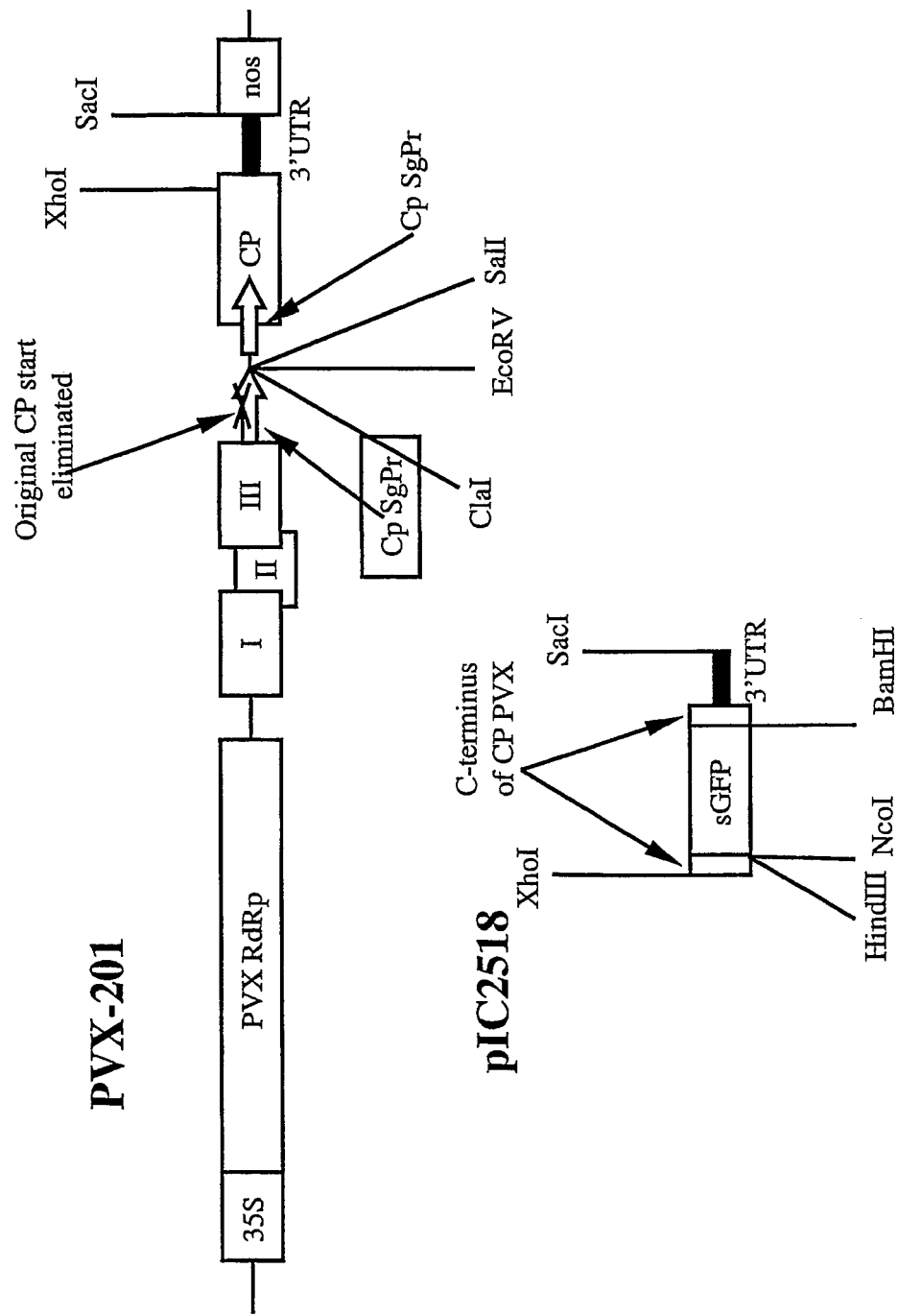
FIG. 3 depicts basic constructs and cloning strategy used for cloning of the cDNA of a PVX-based precursor vector.

At the first step an intermediate construct pIC2518 was obtained. This plasmid contains consequently: the C-terminus of CP (62 bp) from the XhoI site to the terminator with a HindIII site introduced right after the termination codon, enhanced GFP (sGFP) gene (starting codon included into NcoI site) and the 3'-terminus of PVX virus including the C-terminus of CP (62 nt), 3'-UTR and s poly (A) sequence followed by a SacI site (FIG. 3).

Two sets of oligonucleotides were synthesized to clone 2 different pairs of donor/acceptor splicing sites:

```
1.
                                              (SEQ ID NO: 1)
D1+ CGAACGGTCGGTAACGGTCGGTAAA
                                              (SEQ ID NO: 2)
D1- TCGACTTTACCGACCGTTACCGACCGTT
                                              (SEQ ID NO: 3)
A1+ AGCTAACCTAGCAGGTTATATGCAGGTTATATGCAGGTC
                                              (SEQ ID NO: 4)
A1- CATGGACCTGCATATAACCTGCATATAACCTGCTAGGTT 2.
                                              (SEQ ID NO: 5)
D2+ CGAAAGGTAAG
                                              (SEQ ID NO: 6)
D2- TCGACTTACCTTT
                                              (SEQ ID NO: 7)
A2+ AGCTAACCTATTGCAGGTTGC
                                              (SEQ ID NO: 8)
A2- CATGGCAACCTGCAATAGGTT
```

After annealing to each other, corresponding oligonucleotides form the following double stranded DNA fragments.

```
D1+/D1- fragment D1         (SEQ ID NOS: 1 and 2)
5' CGAACGGTCGGTAACGGTCGGTAAAG 3'
3' TTGCCAGCCATTGCCAGCCATTTCAGCT 5'
```

```
                      -continued
A1+/A1- fragment A1          (SEQ ID NOS: 3 and 4)
5' AGCTAACCTAGCAGGTTATATGCAGGTTATATGCAGGTC 3'
3' TTGGATCGTCCAATATACGTCCAATATACGTCCAGGTAC 5'

D2+/D2- fragment D2          (SEQ ID NOS: 5 and 6)
5' CGAAAGGTAAG 3'
3' TTTCCATTCAGCT 5'

A2+/A2- fragment A2          (SEQ ID NOS: 7 and 8)
5' AGCTAACCTATTGCAGGTTGC 3'
3' TTGGATAACGTCCAACGGTAC 5'
```

The 5'-protruding ends of the fragments are adhesive to ClaI/SalI restricted DNA in case of D1 and D2. Fragments A1 and A2 can be ligated into HindIII-NcoI sites.

Plasmid PVX-201 described above (FIG. 3) was digested with ClaI and SalI. Then the D1 or D2 fragment was ligated into the digested vector, yielding construct pIC3033 (in case of D1) of pIC3053 (in case of D2).

Plasmid pIC2518 (FIG. 3) was digested HindIII and NcoI. Ligation of fragment A1 or A2 produced construct pIC3041 (A1) or pIC3068 (A2), respectively.

Figure 2:
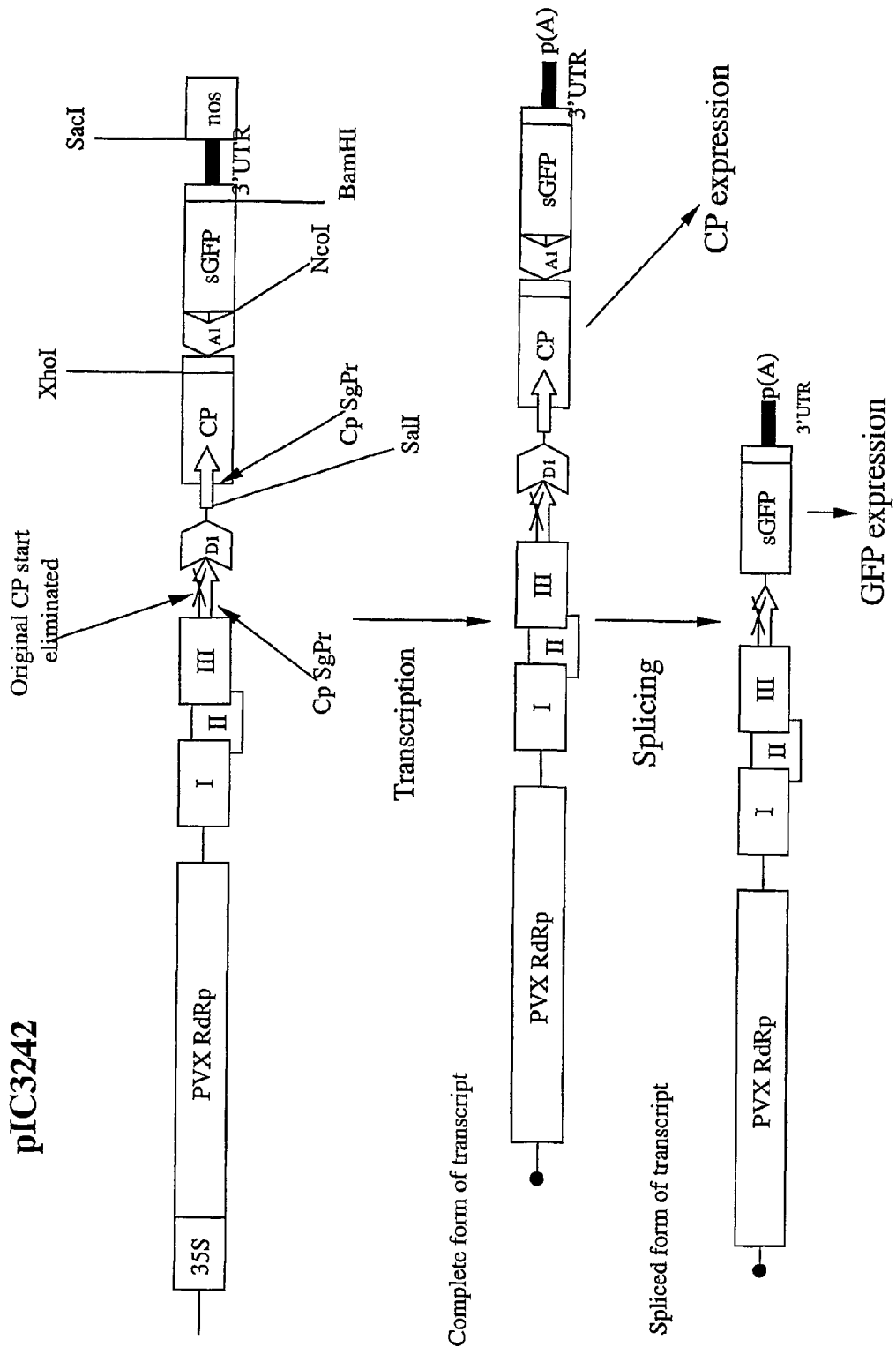
FIG. 2 depicts the structure of a PVX-based precursor vector, its generation by transcription to give the complete form of the transcript and its splicing. Expression can occur from the transcript (precursor vector and replicon) and the spliced transcript (replicon).

Two variants of a spliceable PVX provector plasmid were obtained by cloning of the XhoI-SacI fragment from pIC3041 into pIC3033 and of the XhoI-SacI fragment from pIC3068 into pIC3053. The resulting plasmids were named pIC3242 (splice sites D1+A1) and pIC3258 (splice sites D2+A2) (FIG. 2)

Example 2

Microprojectile Bombardment

Microprojectile bombardment was performed with the Biolistic PDS-1000/He Particle Delivery System (Bio-Rad). Separate *N. benthamiana* leaves were bombarded at 900 psi with 15 mm distance from a macrocarrier launch point to the stopping screen and 60 mm distance from the stopping screen to a target tissue. The distance between the rupture disk and a launch point of the macrocarrier was 12 mm. The cells were bombarded after 4 hours of osmotic pretreatment.

The DNA-gold coating procedure (PEG/Mg) was performed as follows: 25 μl of gold suspension (60 mg/ml in 50% glycerol) was mixed with 10 μl of plasmid DNA (up to 1 μg/μl) in an Eppendorf tube and supplemented subsequently by 10 μl of 40% PEG in 1.0 M $MgCl_2$. The mixture was vortexed for 2 min and than incubated for 30 min at room temperature without mixing. After centrifugation (2000 rpm, 1 min), the pellet was washed twice with 1 ml of 70% ethanol, once by 1 ml of 99.5% ethanol and finally it was dispersed in 30 μl of 99.5% ethanol. Aliquots (6 μl) of DNA-gold suspension in ethanol were loaded onto macrocarrier disks and allowed to dry up for 5-10 min.

Plasmid DNA Preparation

Plasmids were transformed into *E. coli* strains DH10B and JM109, maxi preps were grown in LB medium and DNA was purified using the Qiagen kit.

Example 3

Mechanical inoculation of slants with provector plasmid DNA

Fully developed leaves of five to seven weeks old *Nicotiana benthamiana* plants were inoculated with plasmid DNA by mechanical wounding. For this purpose, 10-50 μg of DNA was mixed with 3×GKP-buffer (50 mM glycine, 30 mM $K_2HPO_4$, 3% celite, 3% benthonite) and scratched gently on the upper side of the leaves.

Example 4

Expression of a Reporter Gene in Plant Leaves by Converted (Spliced) PVX-Based Provector Fully developed *N. benthamiana* leaves were bombarded with plasmids pIC3242 and pIC3258. It was expected that two different RNA transcripts can be synthesized in plant cell from each of these plasmids—complete form and spliced form (see FIG. 2).

The presence of the second transcript can be detected by the GFP fluorescence in a cell transfected with the provector.

Strong GFP fluorescence has been observed in numerous leave cells bombarded with pIC3242 (48 hours after bombardment). No GFP expression was detected in the case of pIC3258—so this construct may serve as a negative control in this experiment. This difference occurred due to the different donor/acceptor sites used in the constructs (see example 1). In the case of pIC3258, a 9-nt sequences that represents splice-site consensus of *Arabidopsis thaliana* was used. In the case of pIC3242, donor and acceptor sites were designed as described in Nussaume et al. *Mol. gen. genet,* 1995, 249:91-101 where they were tested and proved to be active in plants.

Figure 15:
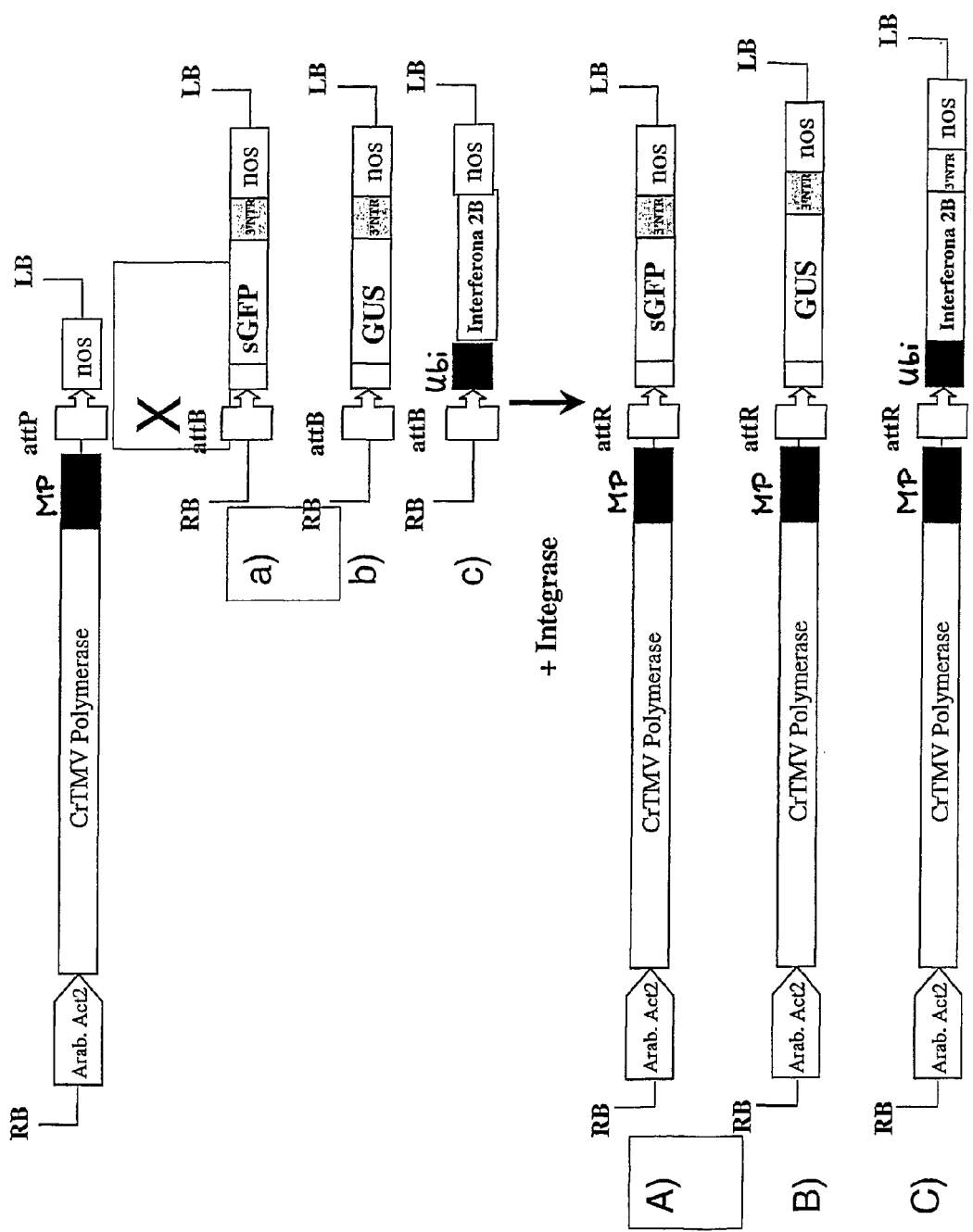
FIG. 15 depicts the general scheme of expression of several genes via CrTMV-based precursor vectors (a-c and vector shown at the top) and generation of replicons (A-C) by using the integrase/att-system for site-specific recombination. The precursor vectors are cloned into binary vectors with T-DNA-borders (LB and RB).

According to several investigations (Fedorkin et al., *J Gen Virol* 2001; 82(Pt 2):449-58, Cruz et al., *Plant Cell* 1998; 10(4):495-510), the CP of PVX is required for viral cell-to-cell transport. In case of the construct pIC3242, the CP gene must be spliced out of RNA. This means that the spliced form of the transcript (FIG. 3) cannot express the CP and provide cell-to-cell movement of the virus. However, in several experiments with pIC3242 not only single cells but also multi-cell loci (10-1000 cells) expressing GFP where detected. This indicates that the splicing of the provector transcript does not occur with 100% efficiency. A fraction of the full length RNA remains unspliced and therefore CP can be expressed from this form of the transcript, while the GFP gene remains silent in this RNA (since no GFP expression was detected in case of pIC3258).

Example 5

Generating Transcenic *N. benthamiana* Plants Expressing Cre Recombinase

The actin2 promoter-LoxP-Cre Orf-Nos terminator fragment from pIC1321 was subcloned as a Not1 blunt-Sac fragment into the SmaI and SacI sites of the binary vector pBIN19, resulting in construct pIC1593 (FIG. 14).

The plasmid pIC1593 was introduced in *Agrobacterium* strain Agl1 by electroporation and transformed *agrobacteria* were used to transform *N. benthamiana*. DNA extracted from 10 transformants was used to test for the presence of the transgene by PCR. All plants were found positive when PCR was performed with primers for the kanamycin transformation marker or for the Cre gene.

Example 6

Generation of Functional Vectors from Provectors Using Site-Specific Recombination a) General Description of the System The system described consists of two core types of CrTMV based vectors which carry LoxP-recombination sites (FIG. 8):

i) Vector type: Polymerase-MP-LoxP: The vector encodes the RdRP of CrTMV and the movement protein (MP), which allows the virus to move from cell to cell, but not to move systemically. The viral transcription is controlled by an *Arabidopsis*-Actin 2 promoter.

ii) Vector type: LoxP-gene of interest-3'NTR-nos-terminator (see FIG. 8a-c): This class of vectors encode a reporter gene (sGFP or GUS) and regulatory elements (nos: nopalin-synthase terminator; 3' NTR: nontranslated region, pseudoknots and tRNA-like structure of CrTMV). The expression of the coat protein (CP; see FIG. 8b) allows the vector to spread systemically in the host plant.

iii) Vector type: Polymerase-MP-attP: See i), with attP-recombination site iiii) Vector type: attB-gene of interest-3'NTR-nos-terminator (see FIG. 15a-c): See ii), with attB-recombination site After recombination catalyzed by Cre-recombinase or integase (via coinfection of a Cre or integrase encoding viral construct) functional units (replions) are formed which are able to express a reporter gene efficiently and are capable of moving from cell-to-cell (FIG. 8A-C, 15 A-C) or systemically (FIG. 8B).

b) Plasmid Construction

Figure 9:
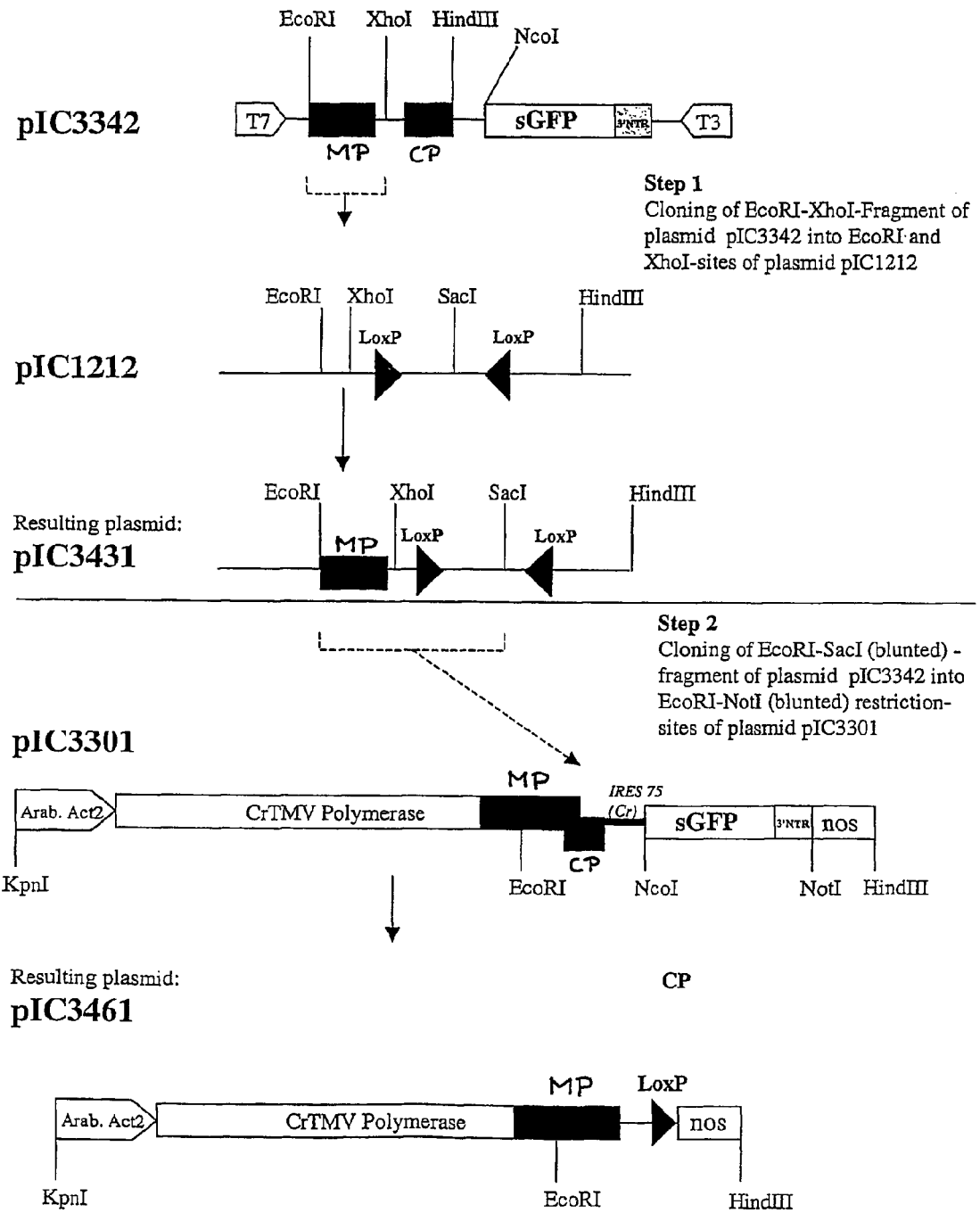
FIG. 9 depicts the cloning scheme of construct pIC3461—a primary component of a recombination system.

A. Cloning of vector type Polymerase-MP-LoxP (FIG. 9)

An EcORI-XhoI-fragment of MP was taken from plasmid pIC3312 (FIG. 5) and was cloned into plasmid pIC1212 which carries two LoxP-sites in opposite orientations. The MP gene of plasmid pIC3342 contains a terminator codon which was introduced 25 AA before the natural stop. In the resulting product pIC3431, a fragment containing part of the MP gene is located next to a LoxP-site. Both elements are isolated via EcORI-SacI restriction. After blunting the SacI restriction site, the fragment was cloned into the vector-containing part of plasmid pIC3301, which contains a single EcORI restriction site in the MP gene. NotI (blunted) was chosen as a second restriction site. In the resulting ligation product (pIC3461) the CP-gene, the IRES-sequence, the gene for sGFP and the 3' nontranslated region of pIC3301 are replaced by LoxP (FIG. 9).

B. Cloning of LoxPReportergene-3'NTR-nos-Terminator Vectors a) Construct LoxP-sGFP-3'NTR-nos (FIG. 8a)

Figure 10:
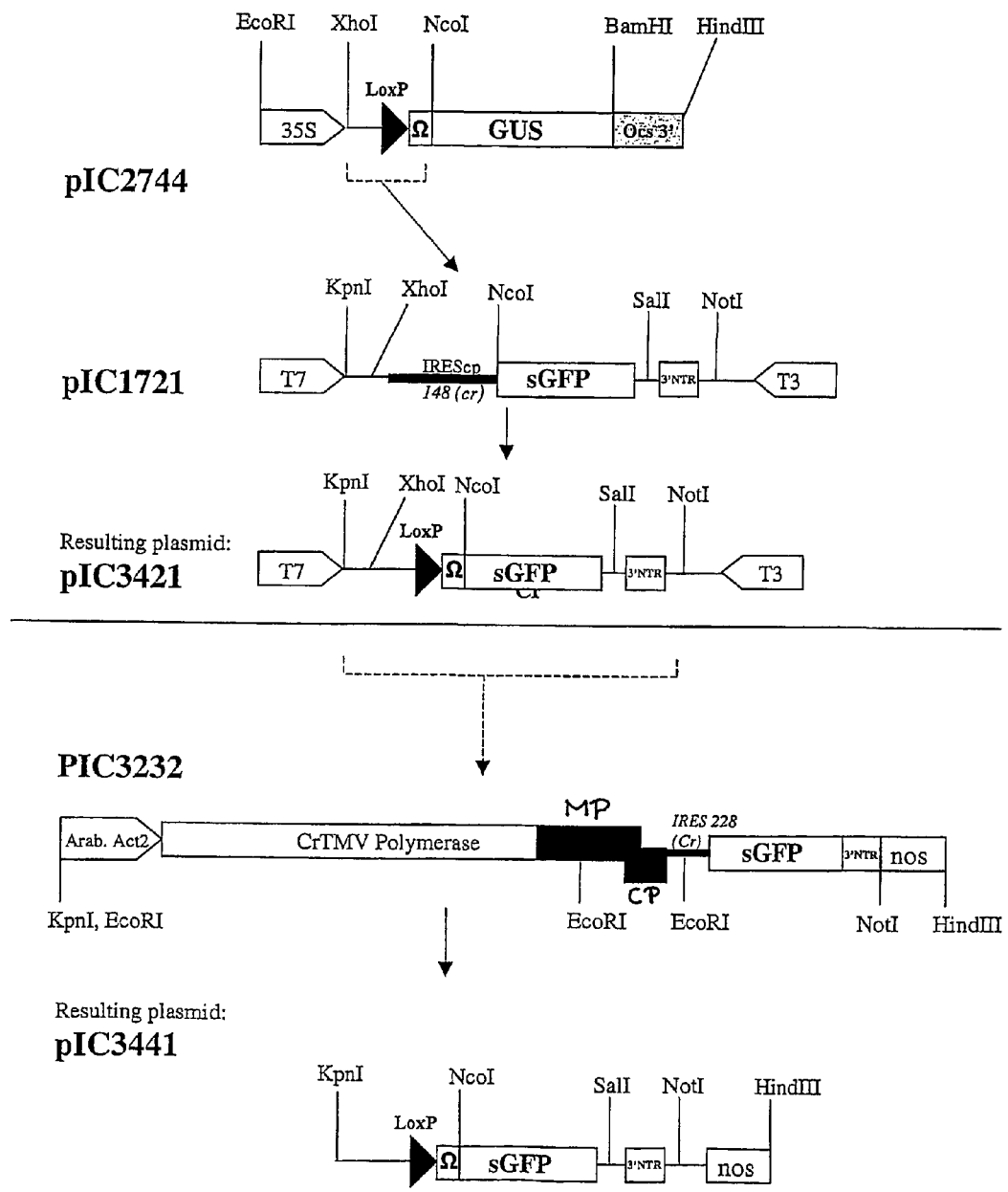
FIG. 10 depicts the cloning scheme of construct pIC3441—one of the secondary components of a recombination system

The XhoI-NcoI-fragment which carries a LoxP-site next to an Ω-leader-sequence was taken from vector pIC2744. In order to place the sequences adjacent to a reporter gene, the fragment was cloned into plasmid pIC1721, which contains the appropriate restriction sites next to a gene for sGFP and a 3'NTR-sequence. Replacement of an IRES-sequence by the fragment let to the resulting plasmid pIC3421. In order to add a nos-terminator-sequence, plasmid pIC3421 was cut by KpnI and NotI. The fragment was introduced into the vector-containing part of plasmid pIC 3232 and the final construct pIC3441 could be obtained (see FIGS. 10 and 8a).

b) Construct LoxP-CP-sGFP-3'NTR-nos (FIG. 8b)

Described above plasmids pIC3342 and pIC1212 were used as starting vectors. The PstI-SacI fragment of pIC3342 that contains the genes for CP and sGFP was cloned into pIC1212. As a result, a LoxP-site is located next to CP and sGFP in the product pIC3451. In order to add a nos-terminator sequence, a similar approach as in case a) was used: An EcORI-NotI-fragment of pIC3451 was introduced into the vector-containing part of pIC3232 resulting in plasmid pIC3491 (see FIG. 11).

c) Construct LoxP-CP-GUS-3'NTR-nos (FIG. 8c)

Figure 12:
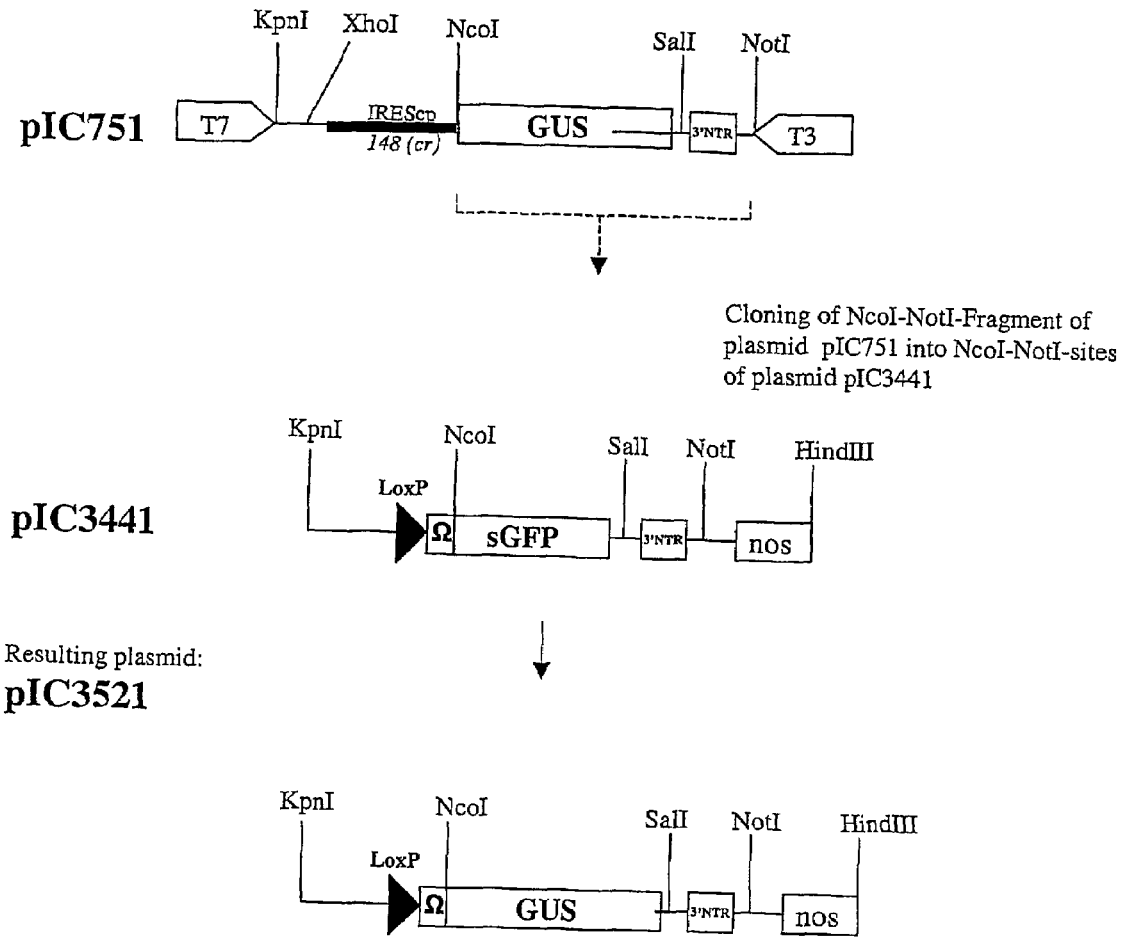
FIG. 12 depicts the cloning scheme of construct pIC3521—one of the secondary components of a recombination system.

Plasmid pIC751 is analogous to pIC1721 and carries a GUS reporter gene instead of sGFP. By cutting with NcoI and NotI the GUS-Gene and the 3'-untranslated region can be directly cloned into pIC3441 hence obtaining the final construct pIC3521 (FIG. 12).

Example 7

Expression of a Single Reporter Gene in Plant Leaves by Converted (Recombined) CrTMV-Based Provector Separate *N. benthamiana* leaves were particle-bombarded with a mixture of three plasmids: pIC3441 (LoxP-GFP, FIG. 10), pIC3461 (Actin2 promoter-CrTMV RdRp-MP-LoxP, FIG. 9) and pIC2721 (Cre-Recombinase under control of hbt promoter). GFP fluorescence was detected in several multicellular loci 38 hours after bombardment. A strong increase of fluorescence and of the size of the infected area were observed during the following days (bombarded leaves where incubated at 25° C. on wet filter paper). No GFP fluorescence was detected in control leaves bombarded with pIC3441 together with pIC2721 without pIC3461.

Example 8

Figure 11:
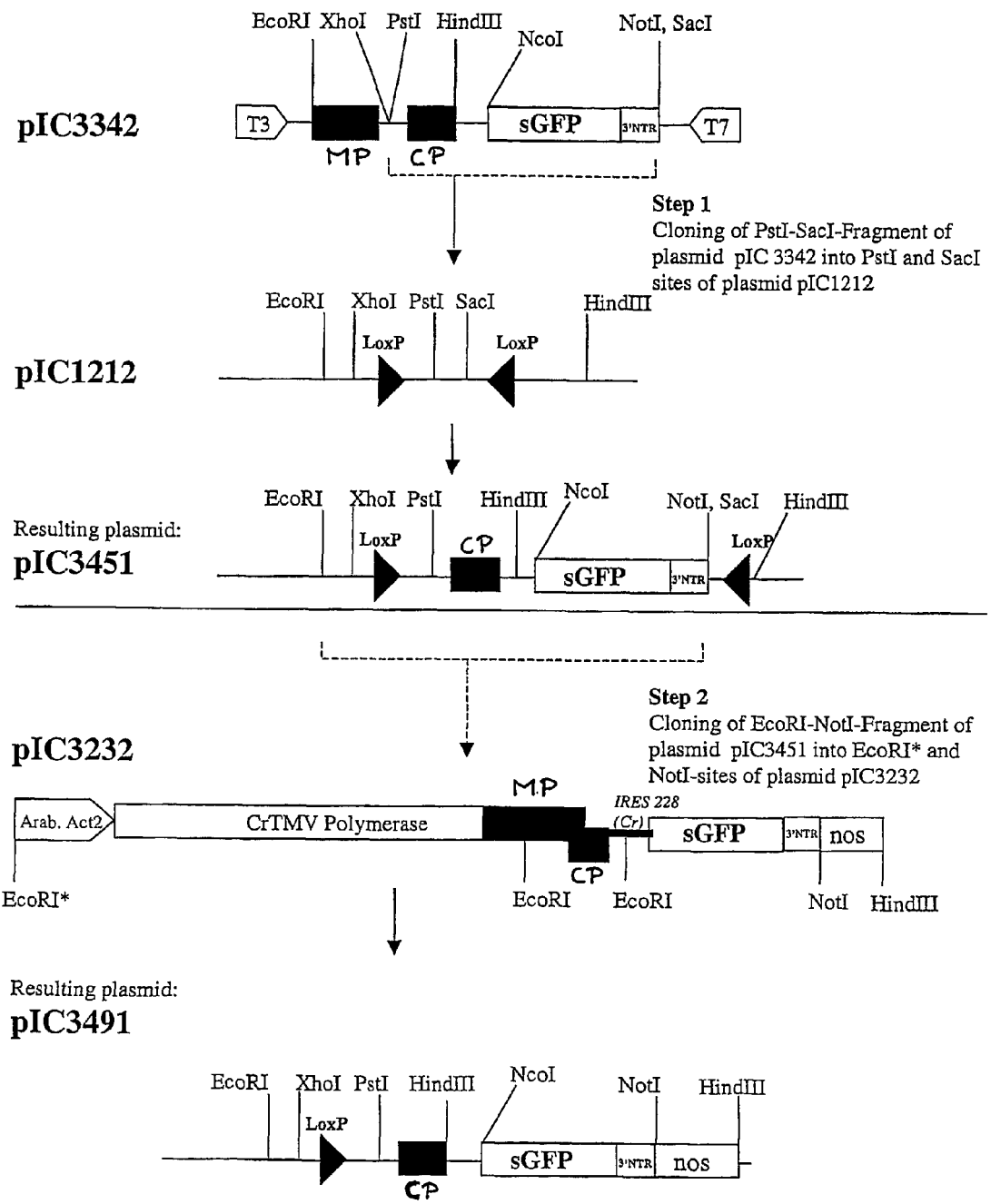
FIG. 11 depicts the cloning scheme of construct pIC3491—one of the secondary components of a recombination system.

Expression of Several Genes in Plant Leaves by Converted (Recombined) CrTMV-Based Provector Separate *N. benthamiana* leaves were particle-bombarded with a mixture of several plasmids:

a) pIC3441 (LoxP-GFP, FIG. 10), pIC3461 (Actin2 promoter-CrTMV RdRp-MP-LoxP, FIG. 9) and pIC2721 (Cre-Recombinase under control of hbt promoter), pIC3521 (LoxP-GUS, FIG. 12).

b) pIC3441 (LoxP-GFP, FIG. 10), pIC3461 (Actin2 promoter-CrTMV RdRp-MP-LoxP, FIG. 9) and pIC2721 (Cre-Recombinase under control of hbt promoter), pIC3491 (LoxP-CP, FIG. 11).

Both reporter genes GFP and GUS were strongly expressed in bombarded leaves in case a). Viral particle formation and systemic movement of the virus are take place in case b).

Example 9

Construction of Spliceable CrTMV-Based Provector

Spliceable provector based on CrTMV virus has certain advantages comparing to PVX-based one. Described in FIG. 4 system allows one to create reporter gene expressing system with the virus, which is fully functional in the infected leaf. Contrary to PVX, coat protein of CrTMV is not required for viral cell-to-cell movement so splicing does no influence on the viral spread in the infected leaf.

A. Cloning of Intermediate Construct pIC3312

A PCR fragment was obtained using cloned cDNA of CrTMV and the following primers:

MPERI+ (corresponds to middle-region of MP including EcoRI site—position 5455 in CrTMV genome):

GTGGTTGACGAATTCGTC                    (SEQ ID NO: 9)

MP− (Complementary to C terminus of MP 17 aa upstream of the natural termination codon introducing artificial terminator with downstream ClaI and XhoI sites. Also this primer contains point mutation of CP ATG into ACG which removes natural start of CP gene without amino acid change in the MP):

(SEQ ID NO: 10)
GGTCTCGAGTTATCGATTATTCGGGTTTGTAATGTTGTAAGACGTTTTC
TTCTTTC

Another PCR fragment was obtained using the same template and the following primers.

CP+ (Corresponds to beginning of CP gene with XhoI and PstI sites introduced upstream of ATG):

(SEQ ID NO: 11)
TAACTCGAGACCTGCAGCATGTCTTACAACATTACAAACCCGAATCAG

CP− (Complementary to C terminus of CP introducing single nucleotide substitution to eliminate NcoI site in CP gene. Also this primer introduces HindIII and NcoI restriction sites downstream of CP gene):

(SEQ ID NO: 12)
CTACTCCATGGTCAAGCTTAAGTAGCAGCAGCAGTAGTCCACGGCACC

Figure 5:
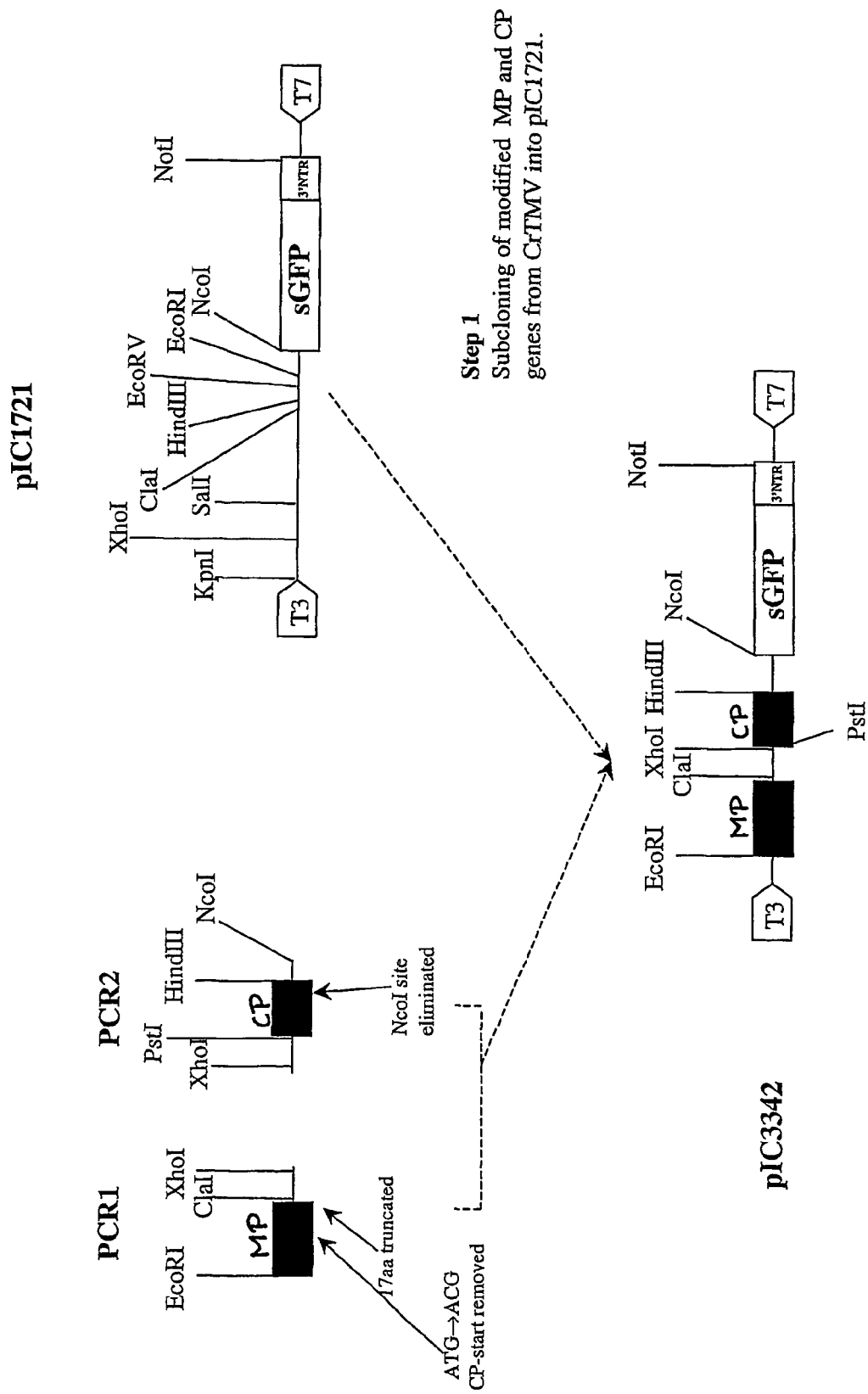
FIG. 5 depicts the cloning strategy of intermediate construct pIC3342.

First, the PCR fragment was digested with EcORI and XhoI enzymes. Second, XhoI and NcoI digested fragments were ligated together into vector pIC1721 (FIG. 5) by EcORI and NcoI sites yielding plasmid pIC3151 (FIG. 5). Then pIC3151 was digested KpnI—EcORV, the KpnI site was blunted with T4 DNA polymerase and the cut plasmid was selfligated to eliminate the sites between KpnI and EcORV. The resulting plasmid was named pIC 3312 (see FIG. 5).

B. Cloning of Spliceable Provector pIC3393 and Control Construction PIC3401

Figure 6:
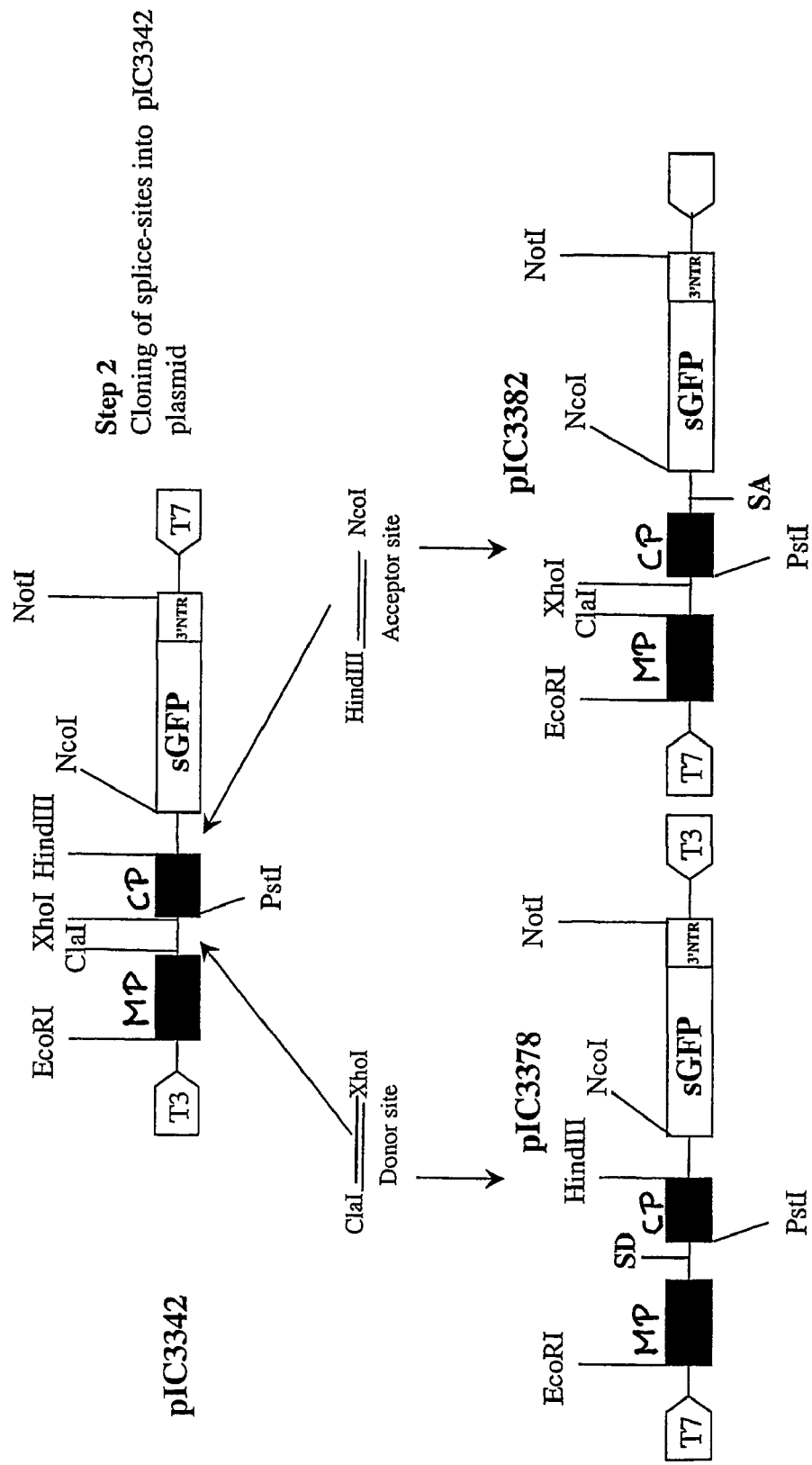
FIG. 6 depicts the cloning strategy of intermediate constructs pIC3378 and pIC3382.

The dsDNA fragments described in example 1 containing donor and acceptor splice sites were cloned into pIC3312 using ClaI and XhoI sites in the case of donor and HindIII and NcoI in case of acceptor splice sites (see FIG. 6). The obtained plasmids were named pIC3378 (donor site) and pIC3382 (acceptor site).

Figure 7:
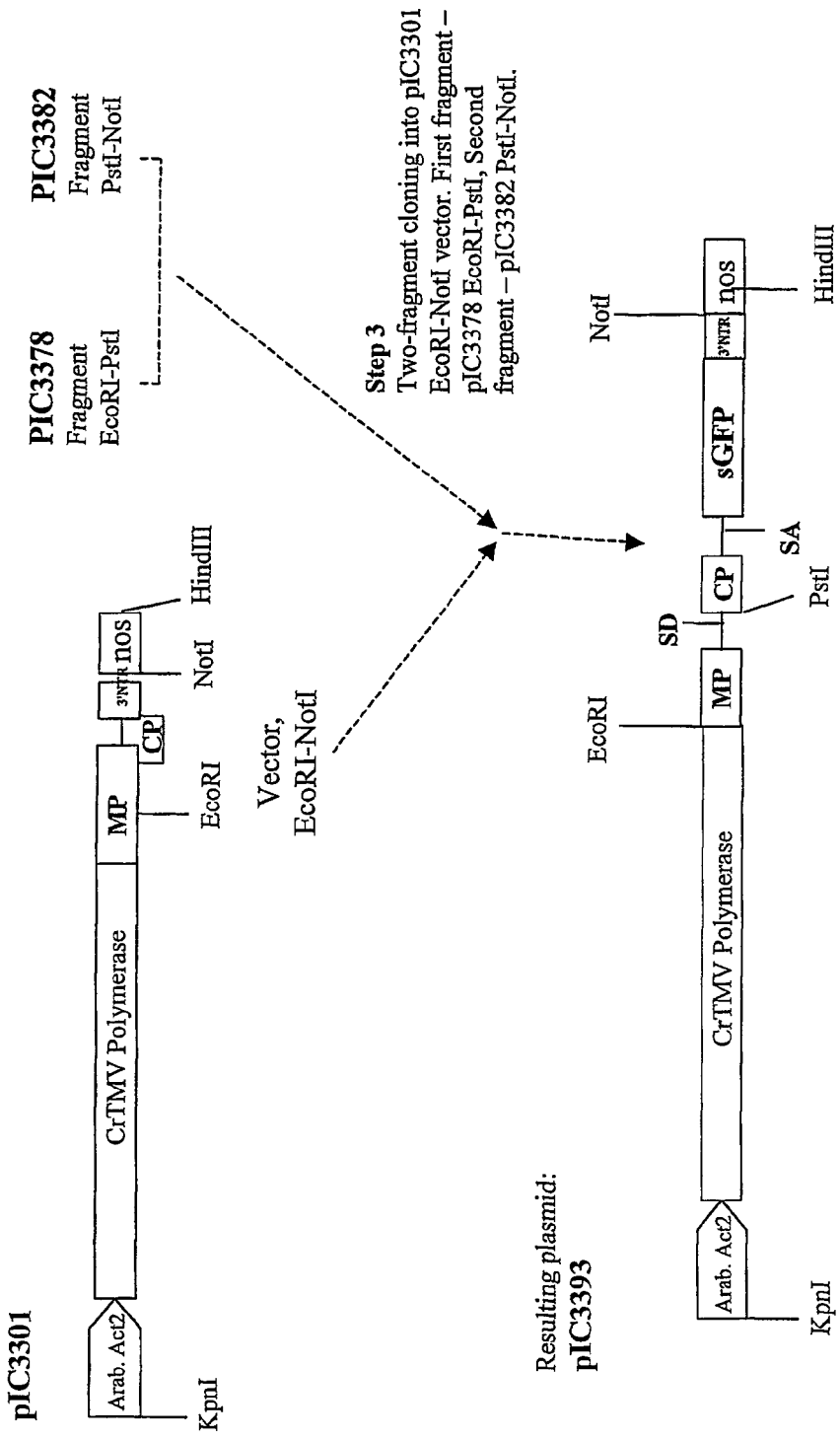
FIG. 7 depicts the final stages of cloning plasmid pIC3393.

To obtain a negative control construct, pIC3401 EcOR1-NotI fragment from pIC3382 was cloned into pIC3301 (FIG. 7).

The final construct pIC3393 was obtained in two-fragment cloning using the EcORI-PstI fragment from pIC3378 with the PstI-NotI fragment from pIC3382 and pIC3301 digested EcORI and NotI as a vector (FIG. 7).

Example 10

Expression of Reporter Gene in Plant Leaves by Converted CrTMV-Based Spliceable Provector Separate N. benthamiana leaves were particle-bombarded with plasmids pIC3393 and pIC3401. GFP fluorescence was detected in several multi-cellular loci 48 hours after bombardment in case of pIC3393. No GFP fluorescence appeared in leaves bombarded with control construct pIC3401.

Example 11

Expression of One Gene of Interest from Viral Vector Assembled from Two CrTMV-Based Provectors Through Site Specific att/Integrase-Based Recombination System a) General Description of the System The system described consists of two core types of CrTMV based vectors which carry attB- or attP-recombination sites (FIG. 15):

i) Vector type: Polymerase-MP-attP: The vector encodes the RdRp of CrTMV and the movement protein (MP), which allows the virus cell to cell, but not systemic movement. The viral transcription is controlled by an *Arabidopsis*-Actin 2 promoter.

ii) Vector type: attB-gene of interest-3'NTR-nos-terminator (see FIG. 15a-b): This class of vectors encodes a reporter gene (sGFP or GUS) and regulatory elements (nos: nopalin-synthase terminator; 3' NTR: nontranslated region, pseudoknots and tRNA-like structure of CrTMV).

iii) Vector type: attB-ubiquitin-gene of interest-3'NTR-nos-terminator (see FIG. 15c): In order to obtain a defined protein which can be isolated from plants, an ubiquitin-cleavage-signal-sequence was introduced between the attB-recombination-site and the downstream located gene of interest (e.g. GFP, Interferona2B, Insulin or Somatotropin). By using this system, any amino acid except prolin can be chosen as the first amino acid of the synthesized protein.

After recombination catalyzed by the integrase-enzyme (via coinfection of a integrase-encoding viral construct), functional units (replicons) are formed which are able to express the gene of interest efficiently and are capable of cell-to-cell movement (FIG. 8A-C).

b) Plasmid Construction

A) Cloning of Vector Type: Polymerase-MP-attP (FIG. 16)

Figure 16:
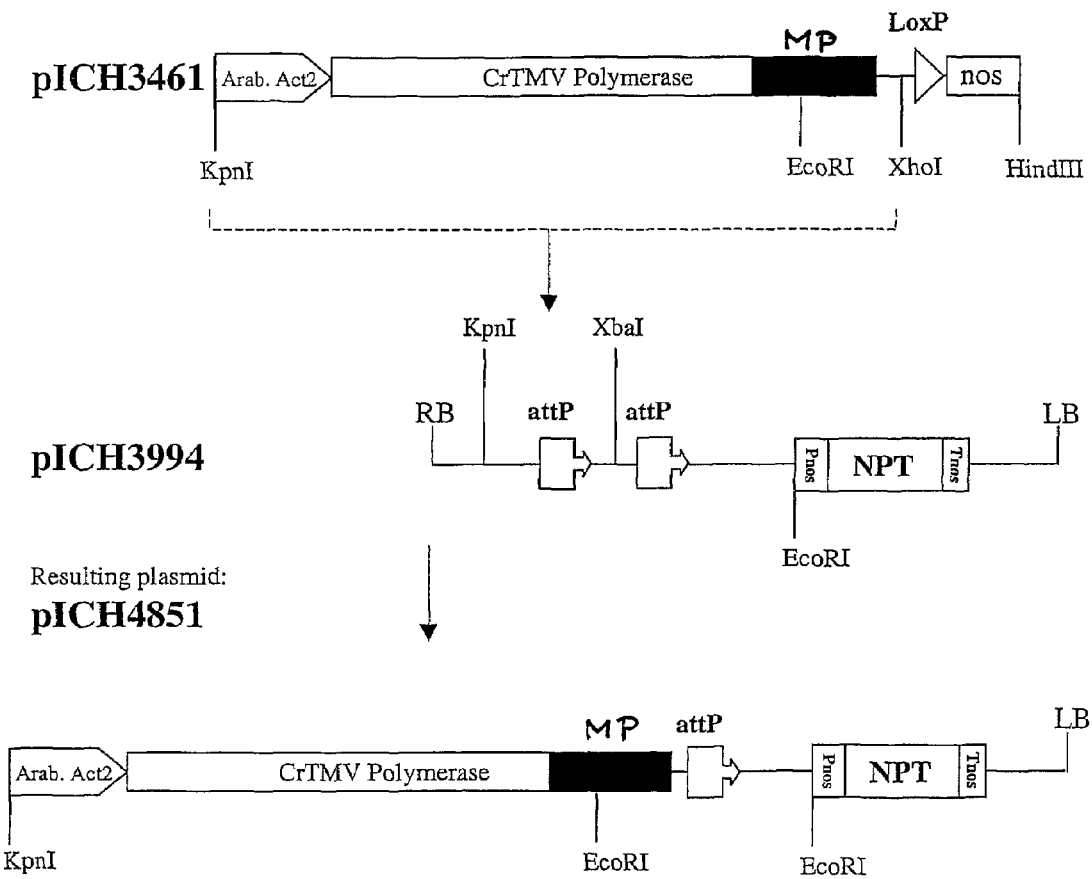
FIG. 16 depicts the cloning scheme of construct pICH4851—one of the secondary components of the recombination system.
Figure 17:
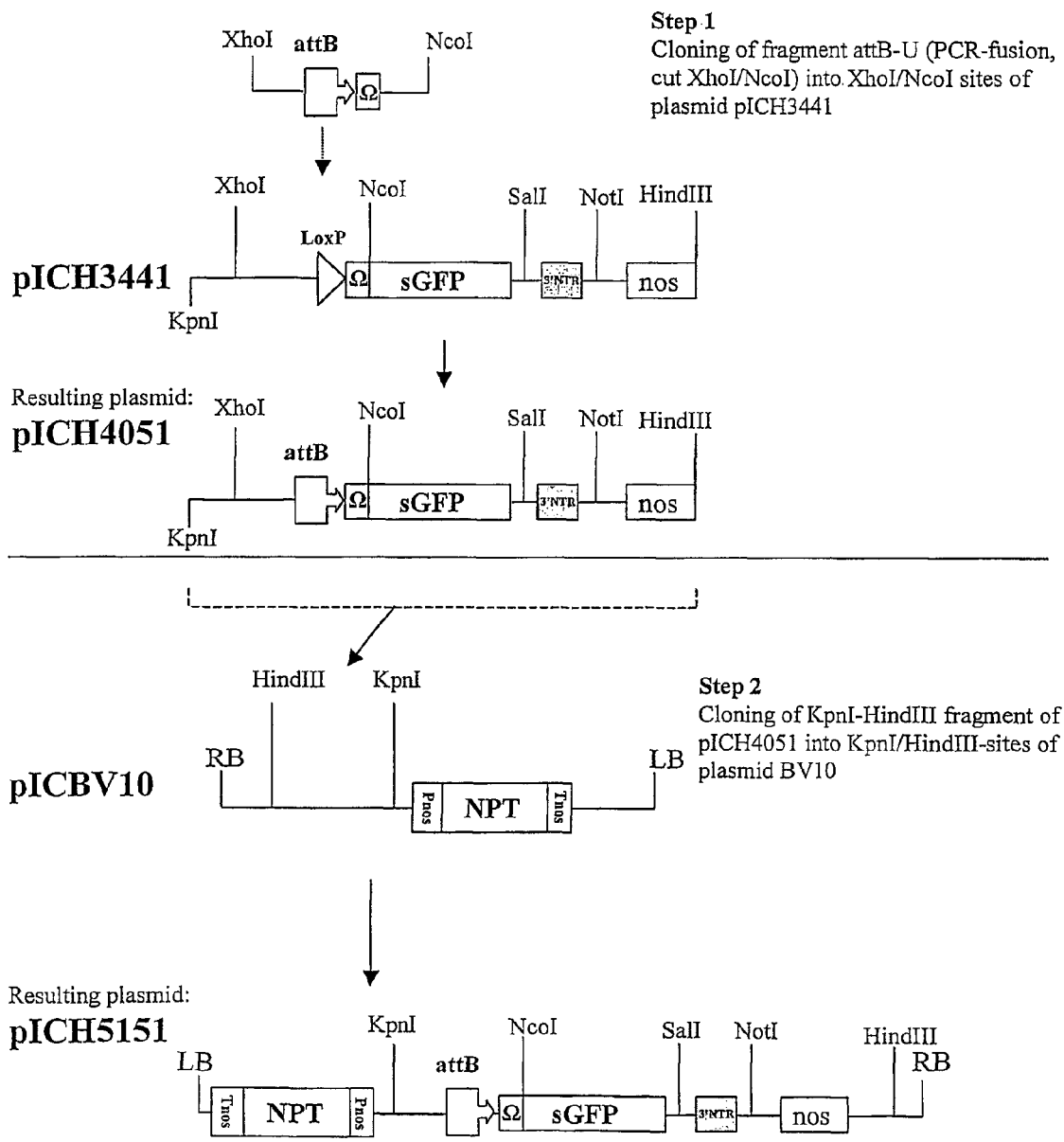
FIG. 17 depicts the cloning scheme of construct pICH5151—one of the secondary components of the recombination system.
Figure 18:
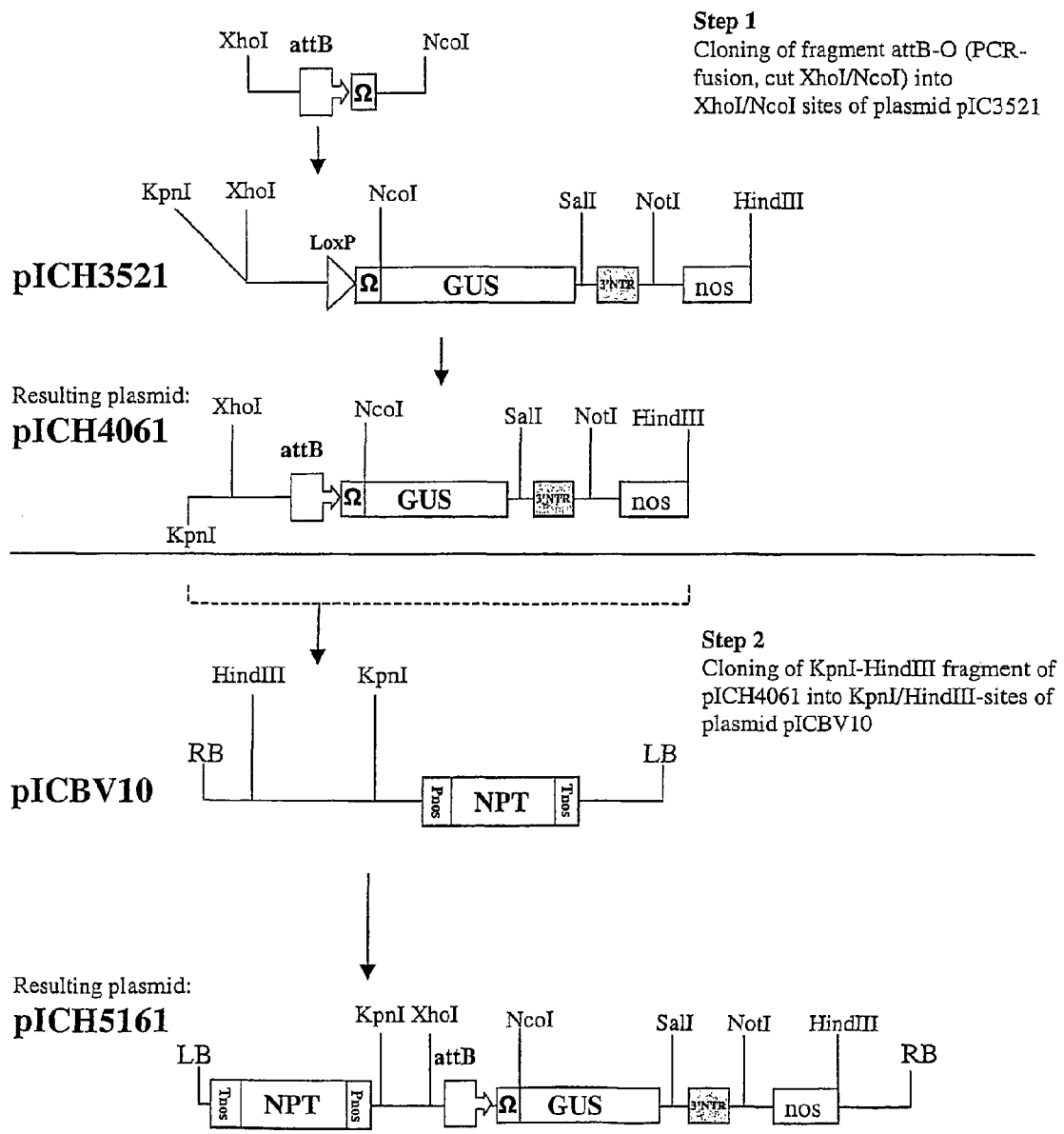
FIG. 18 depicts the cloning scheme of construct pICH5161—one of the secondary components of the recombination system.
Figure 19:
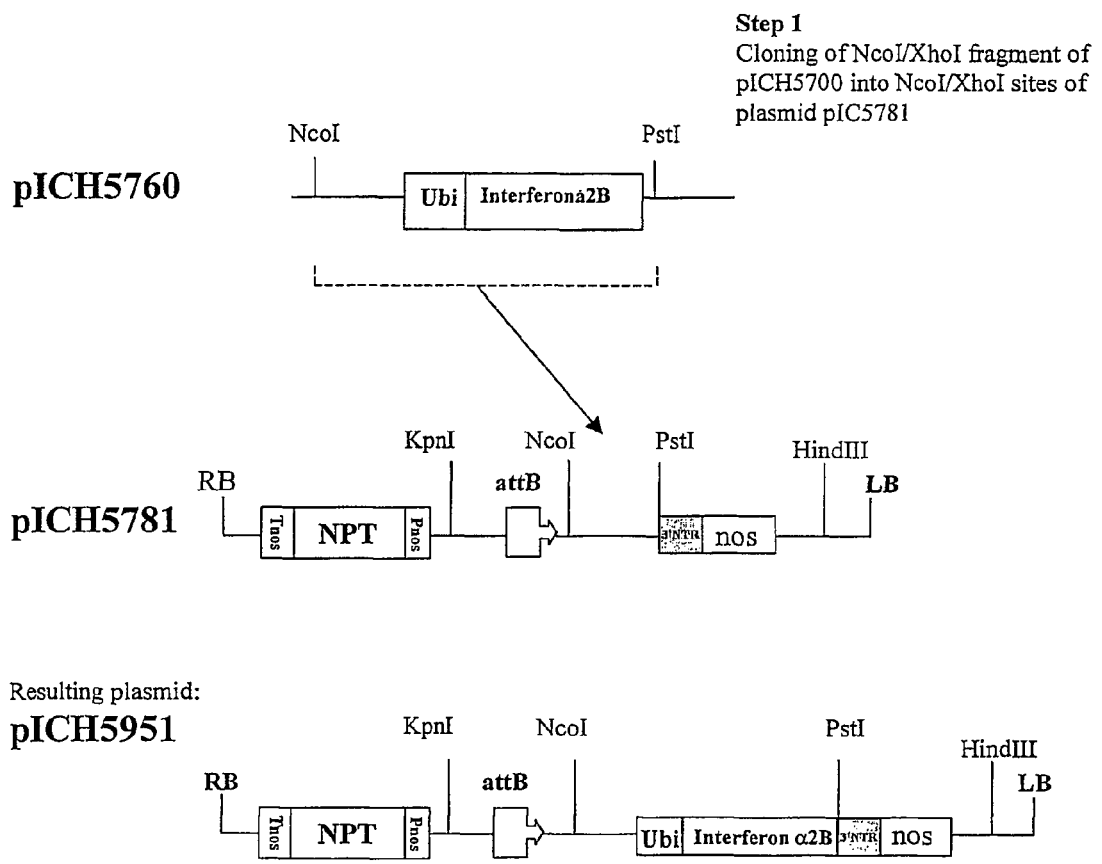
FIG. 19 depicts the cloning scheme of construct pICH5951—one of the secondary components of the recombination system.
Figure 20:
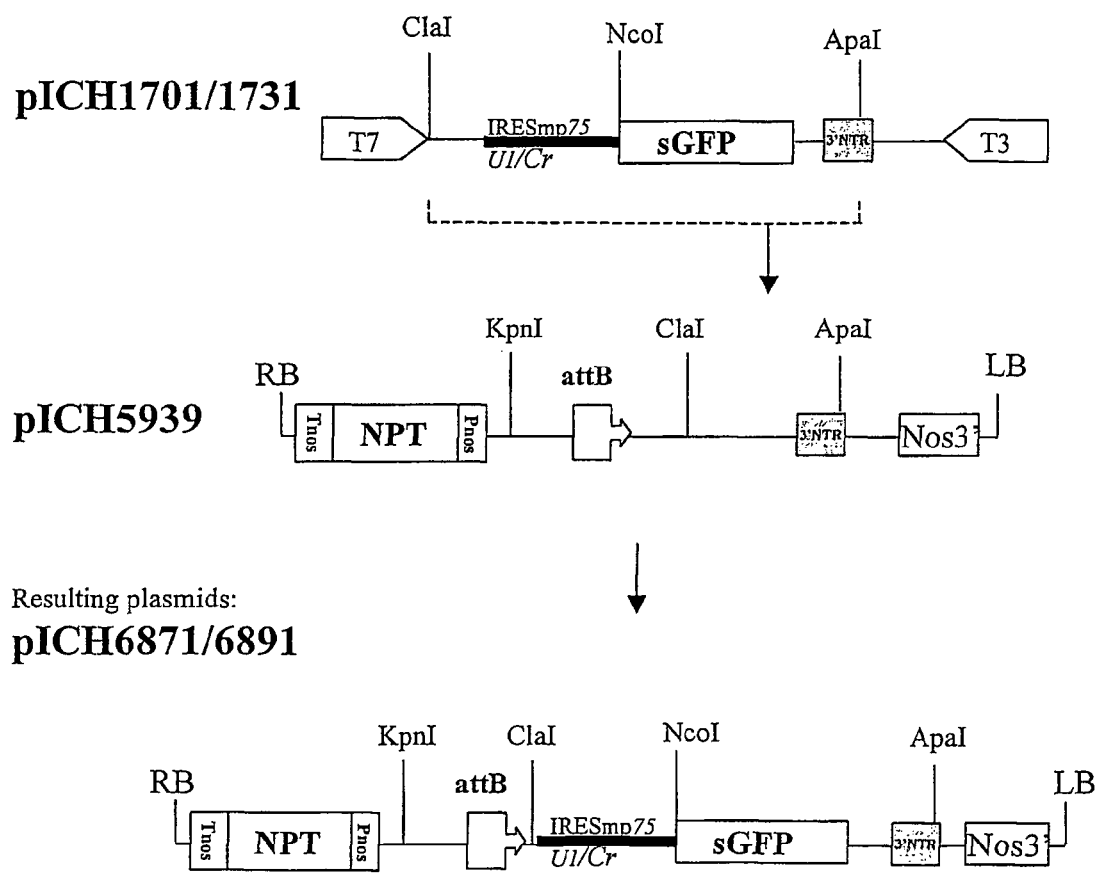
FIG. 20 depicts the cloning scheme of the constructs pICH6871 and pICH6891—two of the secondary components of the recombination system.

An KpnI-XhoI-fragment fragment was taken from plasmid pIC3461 (FIG. 16). After blunting the XhoI-restriction-site, the fragment was cloned into the binary vector pIC3994 which carries two attB-sites in direct orientations, left- and right-T-DNA-borders (LB and RB) and a Kanamycin-expression-cassette as a plant transformation marker. Like the analogous clone from the Cre/Lox-system, the resulting plasmid pICH4851 carries an MP gene with a terminator codon which was introduced 25 AA before the natural stop.

B. Cloning of the Vector-Type: attB-Gene of Interest-3'NTR-nos-Terminator (FIGS. 17-20)

a) Construct attB-sGFP-3'NTR-nos

| Primer combination A) | |
|---|---|
| attB Xho (+): | ATCACTCGAGCTCGAAGCCGCGGTGCGGGT (SEQ ID NO: 13): Complementary to the 5'-part of attB and carrying an XhoI-restriction site at the 5'-terminus |
| attB Ω (−): | GGTAATTGTTGTAAAAATACGATGGGTGAAGGTG GAGTACG (SEQ ID NO: 14): The 3'-part of the primer corresponds to the 3'-region of the attB-sequence, the 5'-part contains 20 nucleotides with complementarity to the 5'-part of the Ω-element. |

Primer combination A was used on an attB-containing template in order to create a PCR product which consists of the complete attB-sequence, 20 Nt of the Ω-leader sequence and an XhoI-restriction site at the 5'-end.

| | |
|---|---|
| attB Ω(+): | CGTACTCCACCTCACCCATCGTATTTTTACAA CAATTACC (SEQ ID NO: 15):<br>The 3'-part of the primer corresponds to the 5'-region of the Ω-sequence, the 5'-part contains 20 nucleotides with complementarity to the 5'- part of the attB-element. |
| Ω NcoI (−): | CATGCCATGGGTAATTGTAAATAGTAATTGTA ATGTT (SEQ ID NO: 16):<br>Complementary to the 3'-part of Ω and carrying an NcoI-restriction site at the 5'-terminus |

Primer combination B) was used on an Ω-sequence-containing template in order to create a PCR-product which contains the complete sequence of the Ω-leader, 20 Nt of the attB-recombination site and a NcoI-restriction-site at the 3'end.

After obtaining PCR products from primer combination A) and B), the isolated oligonucleotides were used together as templates for a PCR-reaction by using the primers attB XhoI (+) and Ω NcoI (−). As a final PCR-product, a fusion of the attB-recombination- and Ω-leader-sequence could be synthesized. This fragment contains XhoI- and a NcoI-restriction sites at its termini. The PCR-product was isolated, digested and cloned into the XhoI- and NcoI-sites of plasmid pICH3441 in order to replace the LoxP-Ω-fusion. The intermediate plasmid was treated with KpnI and HindIII. By inserting this fragment into the corresponding sites of the binary vector BV10, a attB-sGFP-3'NTR-nos vector could be obtained which is transformable into Agrobacterium (pICH5151, see FIG. 17).

A similar approach was used for cloning an analogous provector with the reporter gene GUS. The above described PCR-fragment was cloned into the XhoI- and NcoI-sites of the GUS-containing plasmid pICH3521 resulting in plasmid pICH4061. Finally, a KpnI-HindIII-fragment of plasmid plasmid pICH4061 was ligated into the binary-vector BV0, resulting in the final vector pICH5161 which is capable of stable Agrobacterium-transformation (pICH5161, see FIG. 18).

C) Construction of a attB-Ubiquitin-Interferon-Containing 3'-Provector

In order to clone a fusion of a ubiquitin-sequence and interferon αc2B into an attB-3'-provector, both sequences were synthesized as a fusion and cloned into pUC19 (obtaining plasmid pUC5760). The vector was digested with NcoI and PstI and the resulting fragment was ligated into the corresponding restriction-sites of plasmid pICH5781. The resulting plasmid pICH5951 contains an attB-recombination site, the ubiquitin-interferon fusion, an 3' nontranslated region, a nos promoter and a Kanamycin-expression-cassette. All said sequences are flanked by T-DNA borders (LB and RB, see FIG. 19).

D) In order to replace the Ω-sequence by different IRES-elements which can serve as translational enhancers, a ClaI/ApaI-fragment was taken from plasmid pIC1701 (that contains IRES$_{mp}$75(U1)) or pICH1731 (contains IRES$_{mp}$75(cr)), respectively. The fragments were cloned into the plasmid pICH5939 (similar to plasmid pICH5781, but without NcoI-restriction-site with ATG-sequence as transcription initiation-codon). In the final binary vectors (pICH6871, pICH6891), the attB-recombination-site is located adjacent to an IRES-sequence of 75 bp (6871: U1-origin, 6891: CrTMV-origin), a sGFP-reporter gene and the regulatory elements 3'NTR and nos.

E) Cloning of Vector Type Polymerase-MP-LoxP into Binary Vectors

Figure 21:
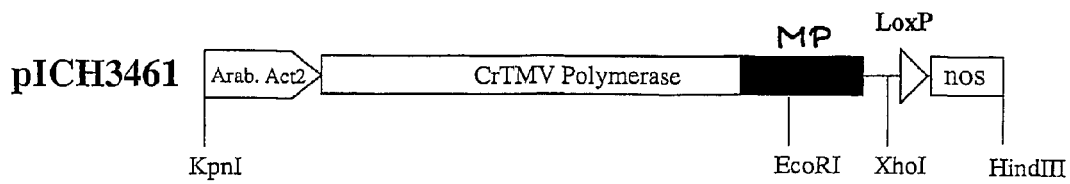
FIG. 21 depicts the cloning scheme of construct pICH4371—one of the secondary components of the recombination system.
Figure 21:
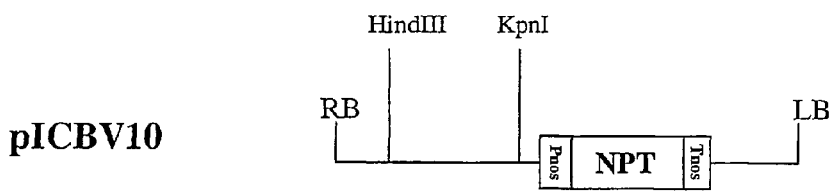
Figure 21:
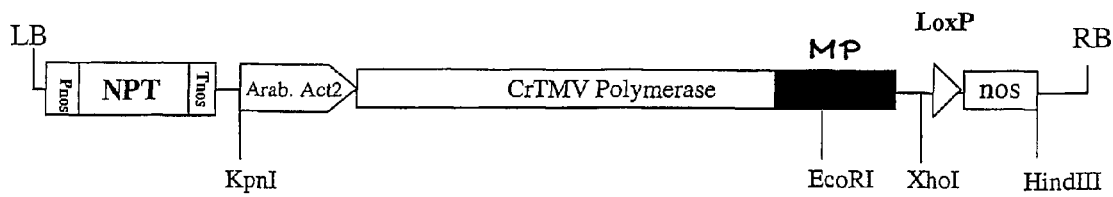

In order to clone the polymerase-MP carrying LoxP-provector into a binary vector, a KpnI/XhoI and a XhoI/HindIII-fragment were ligated together into the vector pICBV10 which was digested with HindIII and KpnI. The resulting plasmid pICH4371 can be stably transformed into Agrobacterium (FIG. 21).

Figure 22:
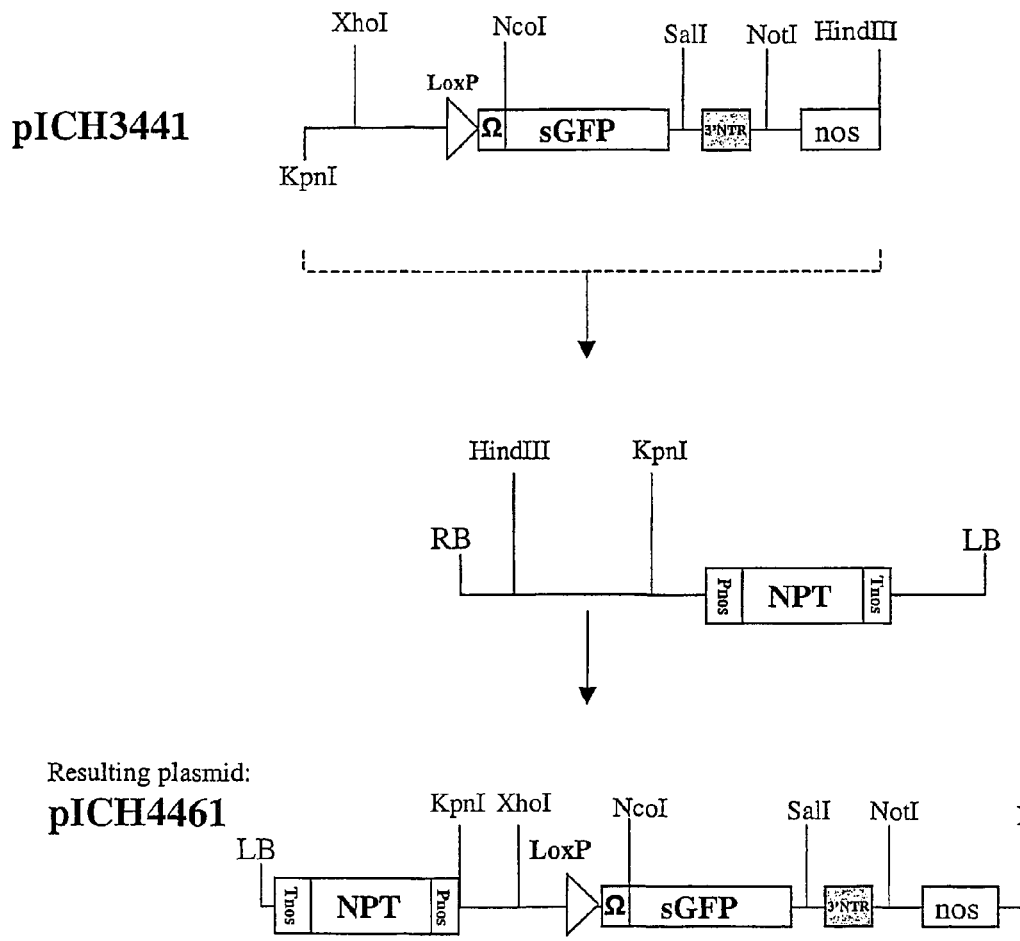
FIG. 22 depicts the cloning scheme of plasmid pICH4461—one of the secondary components of the recombination system.

F) Cloning of Vector Type Loxp-Gene of Interest-3'NTR-Nos-Terminator into Binary Vector An analogous cloning strategy like in E) was used to clone the LoxP-reporter gene provector into a binary vector. Plasmid pICH3441 was digested with the enzymes KpnI and HindIII. The resulting fragment was inserted in the corresponding sides of pICBV10 resulting in the binary plasmid pICH4461 (see FIG. 22).

Example 12

Delivery of Viral Vector Constructs by Infiltration of Agrobacterium tumefaciens Suspension into Plant Leaves of N. benthamiana and N. tabacum All provectors of the Cre/Lox and the integrase/att-system have been cloned into binary vectors which can be transformed stably into Agrobacteria. Hence, DNA-delivery methods alternative to the described techniques are available.

Figure 23:
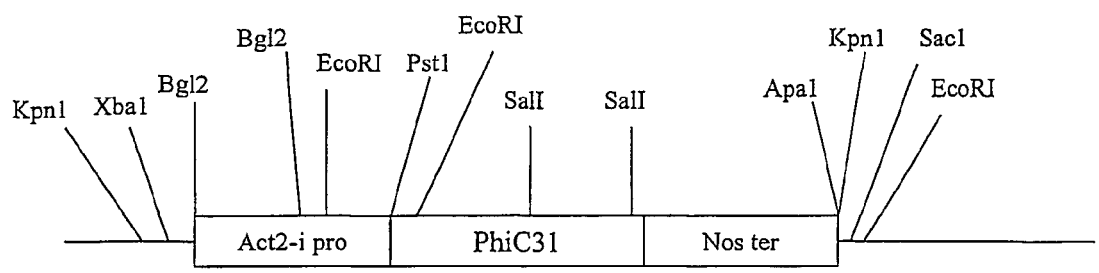
FIG. 23 depicts plasmid pICP1010 which was used as an integrase-source in the att-provector-system.

A very simple delivery method is the infiltration of Agrobacteria suspensions into intact leaves. This so called agroinfiltration was initially developed to analyze foreign gene expression and gene silencing in plants (Kaplia et al., 1997, Plant Science, 122, 101-108; Schöb et al., 1997, Mol. Gen. Genet., 256, 581-588). Agroinfiltration of transgenic tobacco plants was performed according to a modified protocol described by Yang et al., 2000, The Plant Journal, 22(6), 543-551. Agrobacterium tumefaciens strain GV3101 was transformed with individual constructs (pICH4851, pICH5151, pICP1010, FIG. 23) was grown in LB-medium supplemented with Rifampicin 50 mg/l, carbencilin 50 mg/l and 100 µM acetosyringone at 28° C. Agrobacterium cells of an overnight culture (5 ml) were collected by centrifugation (10 min, 4500 g) and resuspended in 10 mM MES (pH 5.5) buffer supplemented with 10 mM MgSO$_4$ and 100 µM acetosyringone. The bacterial suspension was adjusted to a final OD$_{600}$ of 0.8. In case of delivery of several constructs, Agrobacteria suspensions of different constructs were mixed in equal volumes before infiltration.

Agroinfiltration was conducted on near fully expanded leaves that were still attached to the intact plant. A bacterial suspension was infiltrated using a 5 ml syringe. By infiltrating 100 µl of bacterial suspension into each spot (typically 3-4 cm$^2$ in infiltrated area), 8 to 16 spots separated by veins could be arranged in a single tobacco leaf. After infiltration, plants were further grown under greenhouse conditions at 22° C. and 16 h light.

Leaves of N. benthamiana and N. tabacum that were infiltrated with the constructs show expanding sectors of strong GFP-expression 8-12 days after infiltration. The expression could be detected under UV-light directly on the infiltrated leaves. No GFP expression could be observed in case of controls (provector-combination without the integrase-clone).

Example 13

Delivery of Viral Provectors by Infiltration of an *Agrobacterium tumefaciens* Suspension into Plant Leaves of Transgenic Tobacco Plants Expressing the Cre Recombinase (pICH1754)

Leaves of transgenic tobacco plants (transformed construct: pICH1754, species *Nicotiana tabacum*) infiltrated with construct pICH4371 and pICH4461 showed 16 days after infiltration growing sectors of strong GFP-expression which could be observed without microscope under UV-light on intact plants. No GFP-expression was visible on wild type leaves infiltrated with the same *Agrobacteria* suspension mix.

Example 14

The Use of IRES Sequences of Viral Origin (IRES$_{mp}$75 From CrTMV or U1) as Translational Enhancer Sequences The presence of an att- or LoxP-recombination-site between promoter and a downstream located gene limits the efficiency of translation. Therefore, in most cases, it is necessary to use translational enhancing elements to reach an appropriative level of reporter gene-expression in the provector-system. Cloning of the viral IRES sequences IRES$_{mp}$75 (U1) or IRES$_{mp}$75(cr) respectively between the attB-recombination site and GFP clearly increases the expression of the reportergene. Whereas plants, which have been infiltrated with GFP-containing provectors that carry no translational enhancer show nearly no detectable GFP-expression after 10 days, the use of said IRES-sequences led to expression of GFP, which can be detected under UV-light without using a microscope after 5 days. The expression level of gene of interest provided by IRES$_{mp}$75-based translational enhancer activity is comparable or even higher than such provided by "omega" translational enhancer.

The invention claimed is:

1. A process of causing amplification and expression of one or more nucleic acid sequences of interest in a plant, plant tissue, plant cell or cell culture, comprising providing a plant cell with at least two precursor vectors designed for and undergoing processing by site-specific recombination between at least two of said precursor vectors in said cell, whereby due to said processing said plant cell is endowed with at least one replicon which provides(s) for said amplification and expression of said one or more nucleic acids sequences of interest from said at least one replicon.

2. The process according to claim 1, wherein said providing the plant cell with a precursor vector is done by viral transfect ion, Agrobacterium-mediated delivery, particle bombardment, or by conversion of a pre-precursor vector DNA that was pre-integrated into a plant nuclear DNA to form a precursor vector or precursor vectors.

3. The process according to claim 1, wherein said precursor vector is of plant virus origin.

4. The process according to claim 1, wherein said precursor vector is of DNA virus origin.

5. The process according to claim 1, wherein said precursor vector is of RNA virus origin.

6. The process according to claim 1, wherein said processing comprises the production of a set of at least two replicons of type $AB_1, AB_2, \ldots, AB_n$ or of the type $B_1A, B_2A, \ldots, B_nA$ by site specific recombination of a precursor vector (A) with a set of at least two precursor vectors ($B_1, B_2, \ldots, B_n$), wherein n is an integer of $\geq 2$.

7. The process according to claim 1, wherein conditions are provided that facilitate precursor vector processing to give said replicons.

8. The process according to claim 1, wherein said plant cell is of wild type.

9. The process according to claim 1, wherein said plant cell is genetically engineered so as to provide functions necessary for said processing in the plant cell.

10. The process according to claim 9, wherein said plant cell is further genetically engineered so as to provide in trans one or more functions necessary for replicon replication, virus particle assembly, infectivity, suppression of silencing by the host, reverse transcription, cell to cell or long distance movement of said replicons or for recombination or splicing.

11. The process according to claim 9, wherein said genetic engineering of said plant cell is done by transient expression, virus- or *Agrobacterium*-mediated transfect ion, stable integration into genomes of nuclei or organelles or into autonomously replicating plasmids of said plant cell.

12. The process according to claim 1, wherein said recombination of at least two precursor vector molecules results in in vivo assembly of an expressable gene within a replicon, thereby combining different functional gene modules, wherein said different functional gene modules are selected from the group consisting of a promoter, a transcription enhancer, a translation enhancer, a terminator, a coding part of a protein of interest, a signal peptide, a transit peptide, a membrane transport peptide, a purification or visualization of a polypeptide tag, and other fusion proteins, said different functional gene modules originally being located on two or more of said precursor molecules.

13. The process according to claim 1, which results in amplification and/or expression of two or more nucleic acid sequences of interest.

14. The process according to claim 13, wherein said process results in amplification and/or expression of multiple genes of a biochemical pathway or cascade.

15. The process according to claim 1, wherein one or more of said replicons comprise viral capabilities selected from the group consisting of viral particle assembly, infectivity, suppression of gene silencing, reverse transcription, integration into the host chromosome, cell to cell movement, and long distance movement.

16. The process according to claim 1, wherein one of said replicons is essentially a wild type virus which provides in trans conditions necessary for replication of another replicon or replicons.

17. The process according to claim 1, wherein one of said replicons is essentially a helper type virus which provides in trans functions necessary for replication of another replicon or replicons.

18. The process according to claim 1, wherein at least one of said replicons further provides for an expression of products necessary for replicating said replicons.

19. The process according to claim 1, wherein at least one of said replicons further provides for an expression of products necessary for cell-to-cell, long-distance or plant-to-plant movement, suppression of gene silencing, and/or reverse transcription.

20. The process according to claim 18, wherein said products function in trans.

21. The process according to claim 18, wherein said products function in cis.

22. The process according to claim 1, wherein one of said replicons contains an $IRES_{mp}75$ as translational enhancer operably linked to a heterologous nucleic acid sequence encoding a protein of interest.

23. A process for the production of a biochemical product, comprising the amplification and/or expression of one or more nucleic acid sequences of interest according to claim 1.

24. The process according to claim 23, wherein the biochemical product is a protein selected from the group consisting of a pharmaceutical protein and a functional antibody.

* * * * *

UNITED STATES PATENT AND TRADEMARK OFFICE
CERTIFICATE OF CORRECTION

PATENT NO.       : 7,667,092 B2
APPLICATION NO.  : 10/476299
DATED            : February 23, 2010
INVENTOR(S)      : Klimyuk et al.

It is certified that error appears in the above-identified patent and that said Letters Patent is hereby corrected as shown below:

Title Page:
Item 75, Inventors: Please correct "Sylvestre Marillonet"
to read -- Sylvestre Marillonnet --

Column 21, Line 20: Please correct "downstream of CP"
to read -- downstream of the CP --

Claims:
Column 30, Claim 2, Line 58: Please correct "transfect ion"
to read -- transfection --

Column 31, Claim 11, Line 23: Please correct "transfect ion"
to read -- transfection --

Signed and Sealed this

Fifteenth Day of June, 2010

David J. Kappos
*Director of the United States Patent and Trademark Office*

UNITED STATES PATENT AND TRADEMARK OFFICE
CERTIFICATE OF CORRECTION

PATENT NO. : 7,667,092 B2 Page 1 of 1
APPLICATION NO. : 10/476299
DATED : February 23, 2010
INVENTOR(S) : Klimyuk et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1287 days.

Signed and Sealed this

Twenty-eighth Day of December, 2010

David J. Kappos
*Director of the United States Patent and Trademark Office*

```
                        SEQUENCE LISTING

<160> NUMBER OF SEQ ID NOS: 16

<210> SEQ ID NO 1
<211> LENGTH: 26
<212> TYPE: DNA
<213> ORGANISM: Artificial sequence
<220> FEATURE:
<223> OTHER INFORMATION: Synthetic oligonucleotide

<400> SEQUENCE: 1
cgaacggtcg gtaacggtcg gtaaag                                            26

<210> SEQ ID NO 2
<211> LENGTH: 28
<212> TYPE: DNA
<213> ORGANISM: Artificial sequence
<220> FEATURE:
<223> OTHER INFORMATION: Synthetic oligonucleotide

<400> SEQUENCE: 2
tcgactttac cgaccgttac cgaccgtt                                          28

<210> SEQ ID NO 3
<211> LENGTH: 39
<212> TYPE: DNA
<213> ORGANISM: Artificial sequence
<220> FEATURE:
<223> OTHER INFORMATION: Synthetic oligonucleotide

<400> SEQUENCE: 3
agctaaccta gcaggttata tgcaggttat atgcaggtc                              39

<210> SEQ ID NO 4
<211> LENGTH: 39
<212> TYPE: DNA
<213> ORGANISM: Artificial sequence
<220> FEATURE:
<223> OTHER INFORMATION: Synthetic oligonucleotide

<400> SEQUENCE: 4
catggacctg catataacct gcatataacc tgctaggtt                              39

<210> SEQ ID NO 5
```

```
<211> LENGTH: 11
<212> TYPE: DNA
<213> ORGANISM: Artificial sequence
<220> FEATURE:
<223> OTHER INFORMATION: Synthetic oligonucleotide

<400> SEQUENCE: 5
cgaaaggtaa g                                                              11

<210> SEQ ID NO 6
<211> LENGTH: 13
<212> TYPE: DNA
<213> ORGANISM: Artificial sequence
<220> FEATURE:
<223> OTHER INFORMATION: Synthetic oligonucleotide

<400> SEQUENCE: 6
tcgacttacc ttt                                                            13

<210> SEQ ID NO 7
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 7
agctaaccta ttgcaggttg c                                                   21

<210> SEQ ID NO 8
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 8
catggcaacc tgcaataggt t                                                   21

<210> SEQ ID NO 9
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 9
gtggttgacg aattcgtc                                                       18

<210> SEQ ID NO 10
<211> LENGTH: 56
<212> TYPE: DNA
<213> ORGANISM: Artificial sequence
<220> FEATURE:
<223> OTHER INFORMATION: Synthetic oligonucleotide

<400> SEQUENCE: 10
ggtctcgagt tatcgattat tcgggtttgt aatgttgtaa gacgttttct tctttc             56

<210> SEQ ID NO 11
<211> LENGTH: 48
<212> TYPE: DNA
<213> ORGANISM: Artificial sequence
<220> FEATURE:
<223> OTHER INFORMATION: Synthetic oligonucleotide

<400> SEQUENCE: 11
```

```
taactcgaga cctgcagcat gtcttacaac attacaaacc cgaatcag                        48

<210> SEQ ID NO 12
<211> LENGTH: 48
<212> TYPE: DNA
<213> ORGANISM: Artificial sequence
<220> FEATURE:
<223> OTHER INFORMATION: Synthetic oligonucleotide

<400> SEQUENCE: 12
ctactccatg gtcaagctta agtagcagca gcagtagtcc acggcacc                        48

<210> SEQ ID NO 13
<211> LENGTH: 30
<212> TYPE: DNA
<213> ORGANISM: Artificial sequence
<220> FEATURE:
<223> OTHER INFORMATION: Synthetic oligonucleotide

<400> SEQUENCE: 13
atcactcgag ctcgaagccg cggtgcgggt                                            30

<210> SEQ ID NO 14
<211> LENGTH: 41
<212> TYPE: DNA
<213> ORGANISM: Artificial sequence
<220> FEATURE:
<223> OTHER INFORMATION: Synthetic oligonucleotide

<400> SEQUENCE: 14
ggtaattgtt gtaaaaatac gatgggtgaa ggtggagtac g                               41

<210> SEQ ID NO 15
<211> LENGTH: 40
<212> TYPE: DNA
<213> ORGANISM: Artificial sequence
<220> FEATURE:
<223> OTHER INFORMATION: Synthetic oligonucleotide

<400> SEQUENCE: 15
cgtactccac ctcacccatc gtatttttac aacaattacc                                 40

<210> SEQ ID NO 16
<211> LENGTH: 37
<212> TYPE: DNA
<213> ORGANISM: Artificial sequence
<220> FEATURE:
<223> OTHER INFORMATION: Synthetic oligonucleotide

<400> SEQUENCE: 16
catgccatgg gtaattgtaa atagtaattg taatgtt                                    37
```